(12) United States Patent
Albrecht et al.

(10) Patent No.: US 10,377,758 B2
(45) Date of Patent: Aug. 13, 2019

(54) CO-CRYSTALS OF IBRUTINIB WITH CARBOXYLIC ACIDS

(71) Applicant: ratiopharm GmbH, Ulm (DE)

(72) Inventors: Wolfgang Albrecht, Ulm (DE); Jens Geier, Hayingen (DE); Sebastian Rabe, Ulm (DE); David Perez Palacios, Singen (DE)

(73) Assignee: Ratiopharm GmbH, Ulm (DE)

( * ) Notice: Subject to any disclaimer, the term of this patent is extended or adjusted under 35 U.S.C. 154(b) by 0 days.

(21) Appl. No.: 15/559,410

(22) PCT Filed: Mar. 23, 2016

(86) PCT No.: PCT/EP2016/056312
§ 371 (c)(1),
(2) Date: Sep. 18, 2017

(87) PCT Pub. No.: WO2016/156127
PCT Pub. Date: Oct. 6, 2016

(65) Prior Publication Data
US 2018/0072737 A1    Mar. 15, 2018

(30) Foreign Application Priority Data

| Apr. 2, 2015 | (EP) | 15000976 |
| Aug. 3, 2015 | (EP) | 15179523 |
| Nov. 16, 2015 | (EP) | 15020227 |

(51) Int. Cl.
| C07D 487/04 | (2006.01) |
| C07C 51/41 | (2006.01) |
| C07C 51/43 | (2006.01) |
| C07C 55/10 | (2006.01) |
| C07C 57/15 | (2006.01) |
| C07C 63/08 | (2006.01) |
| A61K 31/519 | (2006.01) |

(52) U.S. Cl.
CPC .......... *C07D 487/04* (2013.01); *C07C 51/412* (2013.01); *C07C 51/43* (2013.01); *C07C 55/10* (2013.01); *C07C 57/15* (2013.01); *C07C 63/08* (2013.01); *A61K 31/519* (2013.01); *C07B 2200/13* (2013.01)

(58) Field of Classification Search
CPC .................................................. C07D 487/04
See application file for complete search history.

(56) References Cited

FOREIGN PATENT DOCUMENTS

| WO | WO 2003/074474 A2 | 9/2003 |
| WO | WO 2008/039218 A2 | 4/2008 |
| WO | WO 2013/184572 A1 | 12/2013 |
| WO | WO 2016/160604 | 10/2016 |

OTHER PUBLICATIONS

Caira, Mino R., *Topics in Current Chemistry*, "Crystalline Polymorphism of Organic Compounds", vol. 198, pp. 163-208 (Jan. 1, 1998).
Shan, N. et al., *Drug Discovery Today*, "The role of cocrystals in pharmaceutical science", vol. 13, No. 9-10, pp. 440-446 (May 1, 2008).
As-filed disclosure and file history for U.S. Appl. No. 62/139,599 filed Mar. 27, 2015.

*Primary Examiner* — Brian E McDowell
(74) *Attorney, Agent, or Firm* — Chalin A. Smith; Smith Patent, LLC

(57) ABSTRACT

The present invention relates to co-crystals of ibrutinib, a pharmaceutical composition comprising the same as well as a method of preparing the same.

4 Claims, 15 Drawing Sheets

CO-CRYSTALS OF IBRUTINIB WITH CARBOXYLIC ACIDS

PRIORITY

This application corresponds to the U.S. national phase of International Application No. PCT/EP2016/056312, filed Mar. 23, 2016, which, in turn, claims priority to European Patent Application Nos. 15.000976.9 filed Apr. 2, 2015; 15.179523.4 filed Aug. 3, 2015; and 15.020227.3 filed Nov. 16, 2015, the contents of which are incorporated by reference herein in their entirety.

FIELD OF THE INVENTION

The present invention relates to co-crystals of ibrutinib, a method of preparing the same as well as a pharmaceutical composition comprising the same.

BACKGROUND OF THE PRESENT INVENTION

Ibrutinib (1-[(3R)-3[4-Amino-3-(4-phenoxyphenyl)-1H-pyrazolo[3,4-d]pyrimidin-1-yl] piperidin-1-yl]prop-2-en-1one) has the following chemical structure (I):

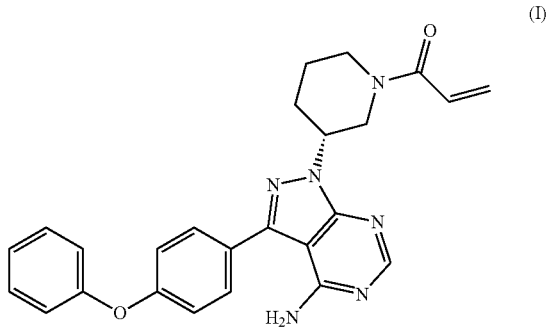 [SMILES: C=CC(=O)N1CCC[C@@H](n2nc(-c3ccc(Oc4ccccc4)cc3)c3c(N)ncnc32)C1]

This pharmaceutically active ingredient is known from WO 2008/039218. Ibrutinib is an inhibitor of bruton's tyrosine kinase (BTK). BTK is a key mediator of at least three critical B-cell pro-survival mechanisms occurring in parallel regulating B-cell apoptosis, cell adhesion and lymphocyte migration and homing. By inhibiting BTK ibrutinib drives B-cells into apoptosis and/or disrupts cell immigration and adherence to tumor-protective microenvironments. Ibrunitib is therefore suitable for treating chronic lymphocytic leukemia (CLL), small lymphocytic lymphoma (SLL) which are B-cell non-hodgkin lymphomas (NHL) and mantle cell lymphoma (MCL). It is marketed in the US under the name Imbruvica.

Crystalline polymorphic forms of ibrutinib are disclosed in WO 2013/184572.

Pharmaceutical formulations comprising ibrutinib are disclosed in WO 20141004707A1.

Ibrutinib has a very low solubility in water e.g. form A of ibrutinib shows according to WO 2013/184572, an observed aqueous solubility of only about 0.013 mg/ml at about pH 8. The solubility strongly depends on the pH. This results in problems in the bioavailability of the active ingredient, first because of the low solubility, and second its solubility depends on the pH value in the stomach of the patient. Particular problems arise from patients wherein the pH value is altered, e.g. due to physiological variability, diseases or premedication such as PP-inhibitors. Ibrutinib has been classified as a BCS class 2 drug and therefore, the absorption and bioavailability is primarily determined by its dissolution under physiological conditions.

WO 2013/184572, discloses further the preparation of six different crystalline forms of ibrutinib base. The existence of amorphous ibrutinib has also been mentioned but no details regarding preparation or properties are described. Three of the crystalline forms, i.e. form A, B and C are anhydrous, non-solvated forms while forms D, E and F contain either methyl isobutyl ketone, toluene or methanol, respectively.

To investigate the impact of crystalline form on physicochemical properties, some crystalline forms of ibrutinib base, i.e. form A, form B, form C as well as amorphous ibrutinib base were prepared and characterized. Form C and amorphous ibrutinib showed substantially higher aqueous solubility compared to form A, but while stirring in suspension, a conversion into the less soluble form A was observed.

Therefore, due to the described complex polymorphism of ibrutinib base and the significant impact of solid state form on dissolution and solubility, new pharmaceutically applicable forms of ibrutinib might be useful as alternative active pharmaceutical ingredients.

Further, amorphous forms may be very difficult to purify since simple process steps like filtration or recrystallization normally do not work. Furthermore, it is very difficult to guarantee content uniformity for the active substance when processed in amorphous form into the final solid formulation. Thus amorphous forms are typically not preferred for production of tablet formulations.

SUMMARY OF THE INVENTION

It has now surprisingly been found that ibrutinib forms stable co-crystals with organic acids which carry one or more carboxylate group(s), or carboxyl amides.

The present invention therefore relates to co-crystals of ibrutinib and a carboxylic acid or carboxylic amide.

Suitable carboxylic acids are for example benzoic acid, fumaric acid and succinic acid as well as those acids exemplified in the description of the method below. Suitable carboxyl amide is for example urea or nicotine amide.

The present invention also relates to a method for preparing co-crystals of ibrutinib comprising the steps of a) suspending ibrutinib with a carboxylic acid in a suitable solvent, preferably an organic solvent, b) heating the obtained suspension till a clear solution is obtained, optionally keeping the temperature for some time and/or under stirring, and c) subsequently cooling the solution of ibrutinib to room temperature, while a solid started to precipitate or started to crystallize. The resulting precipitate or crystals can finally be isolated.

In the method of the present invention in step a) any carboxylic acid can be used which is known to the skilled person. Preferably, a carboxylic acid such as glutamic acid, aspartic acid, malonic acid, adipic acid, nicotinic acid, maleic acid, 3-hydroxybenzoic acid, 4-hydroxybenzoic acid, terephthalic acid, L-tartaric acid, D-tartaric acid, L-malic acid, D-malic acid, succinic acid, oxalic acid, benzoic acid, fumaric acid or citric acid can be used.

In an alternative method of the present invention in step a) any carboxyl amide can be used which are known to the skilled person. Preferably, a carboxyl amide such as urea or nicotine amide can be used.

In the method of the present invention in step a) any suitable solvent for ibrutinib can be used which are known to the skilled person. Preferably, an organic solvent, more preferably a polar organic solvent, such as dichloromethane, chloroform, tetrahydrofuran (THF) or methanol can be used. Most preferably ibrutinib is dissolved in an aliphatic $C_1$-$C_6$ alcohol, such as methanol.

In a further aspect, an organic solvent such as methyl tert.-butyl ether can be used.

In the method of the present invention in step a) the molar ratio of carboxylic acid to ibrutinib is typically equal to or above 1, preferably in the range of 1 to 2, more preferably 1 to 1.5, even more preferred 1 to 1.3, in particular 1 to 1.2, e.g. about 1.

The method of the present invention surprisingly allows preparing co-crystals of ibrutinib preferably in good crystalline quality with advantageous handling properties such as good flowablility, in particular suitable for pharmaceutical compositions, which also have an improved solubility or equal solubility compared to ibrutinib free base.

The method of the present invention surprisingly allows preparing co-crystals of ibrutinib preferably in a single, stable solid form which does not undergo changes in physical characteristics such as different solid forms.

A solid state form may be referred to herein as being characterized by data selected from two or more different data groupings, for example, by a powder XRD pattern having a group of specific peaks; or by a powder XRD pattern as shown in a figure depicting a diffractogram, or by "a combination thereof (or "combinations thereof," or "any combination thereof"). These expressions, e.g., "any combination thereof" contemplate that the skilled person may characterize a crystal form using any combination of the recited characteristic analytical data. For example, the skilled person may characterize a crystal form using a group of three, four or five characteristic powder XRD peaks, and supplement that characterization with one or more additional features observed in the powder X-ray diffractogram, e.g., an additional peak, a characteristic peak shape, a peak intensity, or even the absence of a peak at some position in the powder XRD pattern. Alternatively, the skilled person may in some instances characterize a crystal form using a group of three, four or five characteristic powder XRD peaks and supplement that characterization with one or more additional features observed using another analytical method, for example, using one or more characteristic peaks in a solid state IR spectrum, or characteristics of the DSC thermogram of the crystal form that is being characterized.

Unless indicated otherwise, XRPD peaks are recorded using copper $K\alpha_1/K\alpha_2$ radiation with wavelength 1.5419 Å (weighted mean of Cu $K\alpha_1$ and Cu $K\alpha_2$). Further, unless indicated otherwise, XRPD peaks are reported as degrees 2-theta values with standard errors of ±0.2 degrees 2-theta.

A crystal form may be referred to herein as being characterized by graphical data "as depicted in" a particular figure. Such data include, for example, powder X-ray diffractograms. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the figures herein with graphical data generated for an unknown crystal form and confirm whether the two sets of graphical data are characterizing the same crystal form or two different crystal forms.

In one preferred embodiment the present invention relates to a co-crystal of ibrutinib and benzoic acid (ibrutinib: benzoic acid). Ibrutinib:benzoic acid is characterized by a $^1$H-NMR spectrum showing the following signals (*=signals of benzoic acid): 1.57 (br. s., 1H); 1.84-1.97 (m, 1H); 2.12 (br. s., 1H); 2.25 (qd, J=11.93, 4.11 Hz, 1H); 2.86-3.09 (m, 1H); 3.11-3.26 (m, 1H); 3.30 (br. s., 1H); 3.53-3.77 (m, 1H); 4.06 (d, J=13.29 Hz, 1H); 4.19 (br. s., 1H); 4.54 (d, J=11.34 Hz, 1H); 4.70 (br. s., 1H); 5.57 (d, J=9.78 Hz, 1H); 5.69 (d, J=10.17 Hz, 1H); 6.00-6.21 (m, 1H); 6.51-6.77 (m, 1H); 6.77-7.02 (m, 1H); 7.09-7.19 (m, 5H); 7.39-7.51 (m, 4H (2H*)); 7.54-7.73 (m, 3H (1H*)); 7.91-7.96 (m, 2H)*; 8.24 (s, 1H); 12.93 (br. s., 1H*). A $^1$H-NMR spectrum of ibrutinib benzoic acid is shown in FIG. 1.

In one embodiment of the present invention ibrutinib: benzoic acid is characterized by the following XRPD diffraction peaks: 9.1, 12.1, 13.7, 13.9 and 23.0 or 15.1, 18.2, 21.2, 23.0 and 27.9 or 15.1, 18.3, 21.2, 23.0 and 27.9 degrees 2-theta±0.2 degrees 2-theta.

In a preferred embodiment of the present invention ibrutinib:benzoic acid is characterized further by the following XRPD diffraction peaks: 16.1, 16.2, 19.1, 20.1 and 21.2 or 9.1, 12.1, 22.1, 23.9 and 30.3 or 9.1, 12.1, 22.1, 23.9 and 30.2 degrees 2-theta±0.2 degrees 2-theta.

In a further preferred embodiment of the present invention ibrutinib:benzoic acid is characterized by the following XRPD diffraction peaks: 9.1, 12.1, 13.7, 13.9 and 23.0 degrees 2-theta±0.2 degrees 2-theta and further characterized by one or more peaks at 15.1, 16.1, 16.2, 17.3, 18.2, 19.1, 19.5, 20.1, 21.2, 22.1, 23.9, 24.4, 25.8, 27.9, 28.6, 29.1 and 30.3 degrees 2-theta±0.2 degrees 2-theta.

An XRPD diffraction pattern of ibrutinib:benzoic acid is shown in FIG. 2 and FIG. 3.

In another preferred embodiment the present invention relates to a co-crystal or ibrutinib and fumaric acid (ibrutinib:fumaric acid). Ibrutinib:fumaric acid is characterized by a $^1$H-NMR spectrum showing the following signals (*=signals of fumaric acid): 1.57 (br. s., 1H); 1.75-2.01 (m, 1H); 2.11 (br. s., 1H); 2.18-2.46 (m, 1H); 2.65 (s, 1H); 3.01 (d, J=9.78 Hz, 1H); 3.20 (br. s., 1H); 3.68 (br. s., 1H); 4.06 (d, J=12.12 Hz, 1H); 4.19 (br. s., 1H); 4.52 (br. s., 1H); 4.69 (br. s., 1H); 5.57 (d, J=10.17 Hz, 1H); 5.69 (d, J=11.34 Hz, 1H); 5.99-6.19 (m, 1H); 6.52-6.63 (m, 1H*); 6.64-6.77 (m, 1H); 6.78-6.98 (m, 1H); 7.09-7.19 (m, 4H); 7.31-7.53 (m, 2H); 7.64 (d, J=7.82 Hz, 2H); 8.24 (s, 1H); 13.10 (br. s., 1H*). A $^1$H-NMR spectrum of ibrutinib: fumaric acid is shown in FIG. 6.

In one embodiment of the present invention ibrutinib: fumaric acid is characterized by the following XRPD diffraction peaks: 9.9, 17.4, 18.7, 20.5 and 21.7 or 17.4, 18.2, 20.5, 21.7 and 23.9 degrees 2-theta±0.2 degrees 2-theta.

In a preferred embodiment of the present invention ibrutinib:fumaric acid is characterized further by the following XRPD diffraction peaks: 6.5, 13.0, 18.2, 22.4 and 23.9 or 6.5, 9.9, 25.7, 28.1 and 29.3 degrees 2-theta±0.2 degrees 2-theta.

In a further preferred embodiment of the present invention ibrutinib:fumaric acid is characterized by the following XRPD diffraction peaks: 9.9, 17.4, 18.7, 20.5 and 21.7 degrees 2-theta±0.2 degrees 2-theta and further characterized by one or more peaks at 6.5, 10.1, 10.5, 10.8, 11.9, 12.6, 12.8, 13.0, 14.7, 15.2, 18.2, 19.8, 21.0, 22.4, 25.7, 26.8, 28.1, and 29.3 degrees 2-theta±0.2 degrees 2-theta.

An XRPD diffraction pattern of ibrutinib:fumaric acid is shown in FIG. 7.

In another preferred embodiment the present invention relates to a co-crystal of ibrutinib and succinic acid (ibrutinib:succinic acid). Ibrutinib:succinic acid is characterized by a $^1$H-NMR spectrum showing the following signals (*=signals of succinic acid): 1.57 (br. s., 1H); 1.92 (d, J=13.69 Hz, 1H); 2.12 (br. s., 1H); 2.18-2.32 (m, 1H); 2.38-2.42 (m, 3H*); 2.88-3.07 (m, 1H); 3.10-3.27 (m, 1H); 3.70 (d, J=10.56 Hz, 1H); 4.06 (d, J=13.29 Hz, 1H); 4.19 (br. s., 1H); 4.54 (d, J=12.12 Hz, 1H); 4.69 (br. s., 1H); 5.57 (d, J=9.78 Hz, 1H); 5.69 (d, J=10.56 Hz, 1H); 6.00-6.18 (m, 1H); 6.54-6.77 (m, 1H); 6.77-6.98 (m, 1H); 7.09-7.20 (m, 5H); 7.33-7.51 (m, 2H); 7.65 (d, J=7.82 Hz, 2H) 8.24 (s, 1H); 12.10 (br. s., 1H*). A 1H-NMR spectrum of the ibrutinib:succinic acid co-crystal is shown in FIG. 10.

In one embodiment of the present invention ibrutinib:succinic acid is characterized by the following XRPD diffraction peaks: 17.3, 17.9, 20.2, 21.5 and 21.8 degrees 2-theta±0.2 degrees 2-theta.

In a preferred embodiment of the present invention ibrutinib:succinic acid is characterized further by the following XRPD diffraction peaks: 9.8, 11.5, 13.0, 18.3 and 23.2 degrees 2-theta±0.2 degrees 2-theta.

In a further preferred embodiment of the present invention ibrutinib:succinic acid is characterized by the following XRPD diffraction peaks: 17.3, 17.9, 20.2, 21.5 and 21.8 degrees 2-theta±0.2 degrees 2-theta and further characterized by one or more peaks at 6.5, 9.8, 10.2, 10.8, 11.5, 12.5, 13.0, 14.7, 15.2, 15.7, 18.3, 19.7, 23.2, 23.8, 24.2, 25.1, 26.1, 26.7, 27.2, 28.6 and 29.0 degrees 2-theta±0.2 degrees 2-theta.

An XRPD diffraction pattern of ibrutinib:succinic acid is shown in FIG. 11.

The present invention furthermore relates to a pharmaceutical preparation comprising a co-crystal of ibrutinib according to the present invention, in particular a co-crystal of ibrutinib as defined above. In a preferred embodiment, the present invention relates to a pharmacuetical preparation comprising a co-crystal of ibrutinib with benzoic acid, with fumaric acid or with succinic acid. The pharmaceutical preparation of the present invention preferably is an oral solid preparation, such as a capsule or tablet.

The pharmaceutical preparation can additionally contain one or more pharmaceutically acceptable excipients, such as fillers, binder, glidants, disintegrants, flow regulating agents and release agents. Suitable excipients are for example disclosed in "Lexikon der Hilfsstoffe für Pharmazie, Kosmetik und angrenzende Gebiete", published by H. P. Fielder, 4th Edition and "Handbook of Pharmaceutical Excipients", 3rd Edition, published by A. H. Kibbe, American Pharmaceutical Association, Washington, USA, and Pharmaceutical Press, London.

Suitable fillers are for example lactose and calcium hydrogen phosphate. Fillers can be present in an amount of 0-80% by weight, preferably in an amount of 10-60% by weight of the total weight of the composition.

Suitable binders are for example polyvinylpyrrolidone, hydroxypropyl cellulose, hydroxypropyl methylcellulose, methylcellulose, hydroxyethyl cellulose, sugars, dextran, corn starch. Binders can be present in an amount of 0-80% by weight, preferably in an amount of 10-60% by weight of the total weight of the composition.

Suitable glidants are for example alkaline earth metal salts of fatty acids, like stearic acid. The glidant can be present for example in an amount of 0-2% by weight, preferably in an amount of 0.5-1.5% by weight of the total weight of the composition.

Suitable disintegrants are for example crosscarmelose sodium, sodium carboxymethyl starch, crosslinked polyvinylpyrrolidone (crosspovidone), sodium carboxymethylglycolate (such as Explotab) and sodium bicarbonate. The disintegrant can be present in an amount of 0-20% by weight, preferably in an amount of 1-15% by weight of the total weight of the composition.

A suitable flow regulating agent is for example colloidal silica. The flow regulating agent can be present in an amount of 0-8% by weight, preferably in an amount of 0.1-3% by weight of the total weight of this composition.

A suitable release agent is for example talcum. The release agent can be present in an amount of 0-5% by weight, preferably in an amount of 0.5-3% by weight of the total weight of the composition.

The solid preparation, preferably a tablet or a capsule can be coated, preferably film coated.

A suitable coating agent are for example cellulose derivatives, poly(meth)acrylate, polyvinyl pyrrolidone, polyvinyl acetate phthalate, and/or shellac or natural rubbers such as carrageenan.

The pharmaceutical preparation of the present invention can be prepared by methods well known to a person skilled in the art.

The present invention relates further to the use of a co-crystal of ibrutinib for preparing a pharmaceutical preparation for the treatment of patients with mantle cell lymphoma (MCL), small lymphocytic lymphoma (SLL) and chronic lymphocytic leukemia (CLL).

DETAILED DESCRIPTION OF THE PREFERRED EMBODIMENTS

Figure 1:
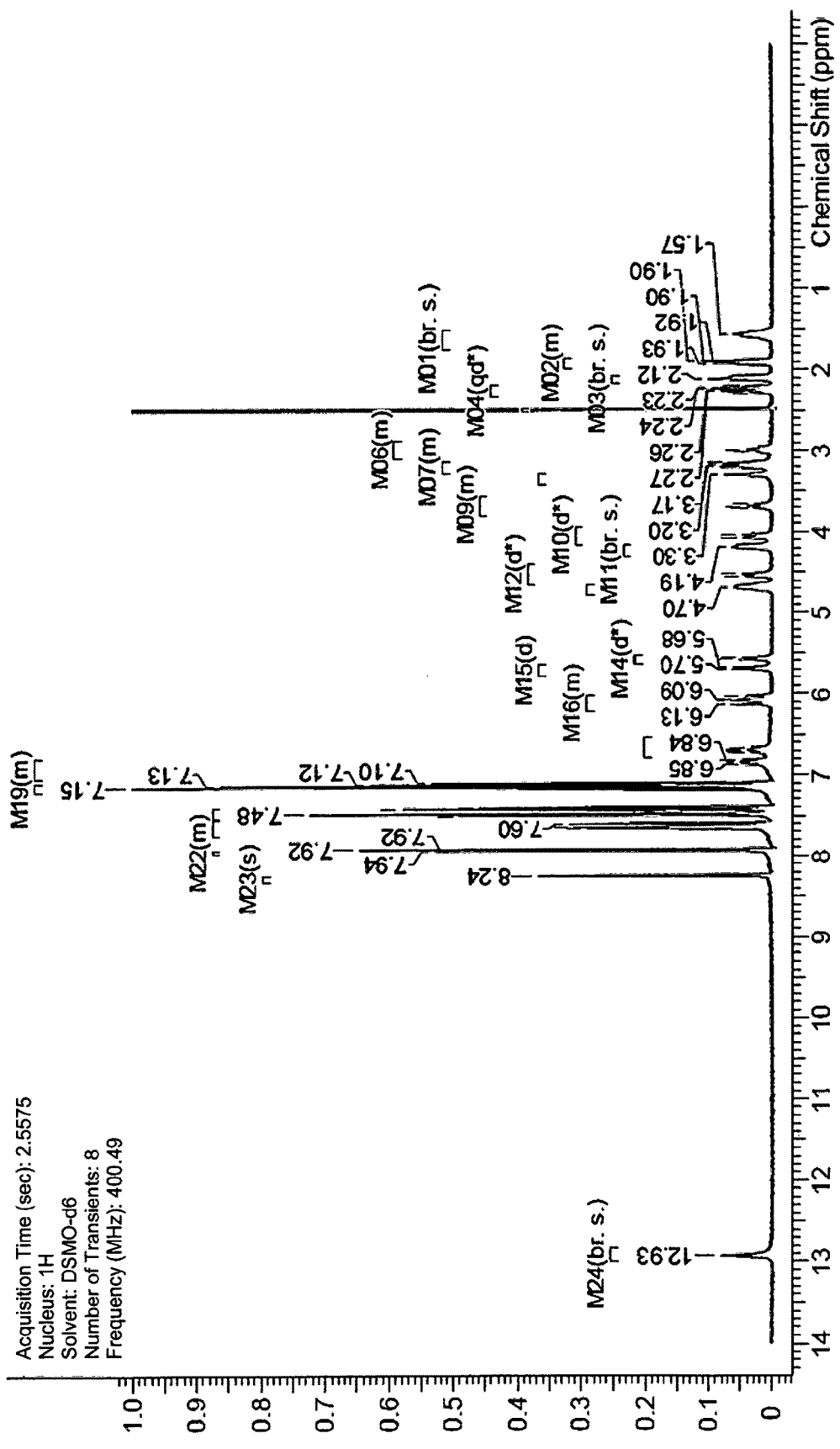
FIG. 1 shows the $^1$H-NMR spectrum of ibrutinib:benzoic acid co-crystal (1:1) ($^1$H-NMR in DMSO-$d_6$, 400 MHz).

Analytical Methods
$^1$H-NMR Spectroscopy
Instrument: Varian Mercury 400 Plus NMR Spectrometer, Oxford AS, 400 MHz.
UHPLC/UV
Instrument: Agilent 1290 Infinity
Wavelength 258 nm
Column: Kinetex C18 150×4.6 mm, 6 µm
Column temp.: 40° C.
Injection volume: 1 µl
Solvent A: acetonitrile
Solvent B: 0.2% formic acid+0.1% heptafluorobutyric acid
Flow: 0.8 ml/min

| time [min] | solvent B [%] |
|---|---|
| 0.00 | 55 |
| 10.00 | 10 |
| 12.00 | 10 |
| 12.50 | 55 |

X-Ray Powder Diffraction (XRPD)
First Method:
The samples were measured on a D8 Advance powder X-ray diffractometer (Bruker AXS, Karlsruhe, Germany) in a rotating PMMA sample holder (diameter: 25 mm; depth: 1 mm) in reflection mode (Bragg-Brentano geometry). Conditions of the measurements are summarized in the table below. Raw data were analyzed with the program EVA (Bruker AXS, Karlsruhe, Germany).

| | |
|---|---|
| radiation | Cu K$\alpha_1$/$\alpha_2$ |
| source | 34 kV/40 mA |
| detector | Vantec-1 (electronic window: 3°) |
| Kβ filter | Ni (diffracted beam) |
| measuring circle diameter | 435 mm |
| detector window slit | 12 mm |
| anti-scatter slit (diffracted beam) | 8 mm |
| divergence slit | v6.00 (variable) |
| Soller slit (incident/diffracted beam) | 2.5° |
| 2θ range | 2° ≤ 2θ ≤ 55° |
| step size | 0.016 |
| step time | 0.2 s |

Second Method (For Stress Testing):
The analysis of was performed on ARL (SCINTAG) powder X-Ray diffractometer model X'TRA equipped with a solid stage detector. Copper radiation of 1.5418 Å was used. Scanning parameters: range: 2-40 degrees two-theta; scan mode: continuous scan; step size: 0.05°, and a rate of 3 deg/min.
X-Ray Singe Crystal Diffraction (XRD)
The crystal was measured on an Oxford Diffraction XCALIBUR diffractometer with area detector at 180 K with a wavelength of 1.54180 Å.
For the following experiments and examples, the starting compound ibrutinib form A was obtained as described in WO 2013/184572.

Example 1: Preparation of Ibrutinib:Benzoic Acid Co-Crystal (1:1)

Experiment 1:
204 mg (0.46 mmol) ibrutinib form A was suspended together with 56 mg (0.46 mmol) benzoic acid in 1 mL MeOH at room temperature (RT). The suspension was heated to 75° C. A clear solution was obtained. The solution was let slowly cooled down to RT while a white solid started to precipitate. The precipitate was isolated by filtration and dried at 50° C./10 mbar for 24 hours (Yield: 65%).

The sample was analysed by means of XRPD and $^1$H-NMR spectroscopy.

Experiment 2:
204 mg (0.46 mmol) ibrutinib form A was suspended together with 56 mg (0.46 mmol) benzoic acid in 1 mL MeOH at 30° C. After stirring, a clear solution was obtained. The solution was let stirring for 60 minutes while a white solid started to precipitate. The precipitate was isolated by filtration and dried at 50° C./10 mbar for 24 hours (Yield: 45%).

The sample was analysed by means of XRPD and $^1$H-NMR spectroscopy.

Experiment 3:
2.4 g (5.5 mmol) ibrutinib form A was suspended together with Benzoic acid 0.67 g (5.5 mmol) in MeOH (50 mL) at 30° C. After stirring of the suspension a clear solution was obtained. The solution was let evaporate in rotavap until an approximately volume of 10 mL. A white solid started to precipitate. The solution was let overnight with stirring at 30° C. for the complete precipitation. It was isolated by filtration and dried at 40° C./10 mbar for 72 hours. (Yield: 68%).

The sample was analysed by means of XRPD and $^1$H-NMR spectroscopy.

The results of Experiments 1 to 3:
$^1$H-NMR Spectroscopy
The sample was analyzed in a 400 MHz-NMR spectrometer. As solvent, DMSO-$d_6$ was used. The $^1$H-NMR spectrum is shown in FIG. 1. The signals are summarized below (*=signals of benzoic acid):

1.57 (br. s., 1H); 1.84-1.97 (m, 1H); 2.12 (br. s., 1H); 2.25 (qd, J=11.93, 4.11 Hz, 1H); 2.86-3.09 (m, 1H); 3.11-3.26 (m, 1H); 3.30 (br. s., 1H); 3.53-3.77 (m, 1H); 4.06 (d, J=13.29 Hz, 1H); 4.19 (br. s., 1H); 4.54 (d, J=11.34 Hz, 1H); 4.70 (br. s., 1H); 5.57 (d, J=9.78 Hz, 1H); 5.69 (d, J=10.17 Hz, 1H); 6.00-6.21 (m, 1H); 6.51-6.77 (m, 1H); 6.77-7.02 (m, 1H); 7.09-7.19 (m, 5H); 7.39-7.51 (m, 4H (2H*)); 7.54-7.73 (m, 3H (1H*)); 7.91-7.96 (m, 2H)*; 8.24 (s, 1H); 12.93 (br. s., 1H*).

The integration values of the 1.93 ppm signal (1H) of ibrutinib and the 2 orto-hydrogens from benzoic acid (7.93 ppm) were 1 and 2 resp. It corresponds with a ibrutinib: benzoic acid=1:1 molar ratio.

Figure 2:
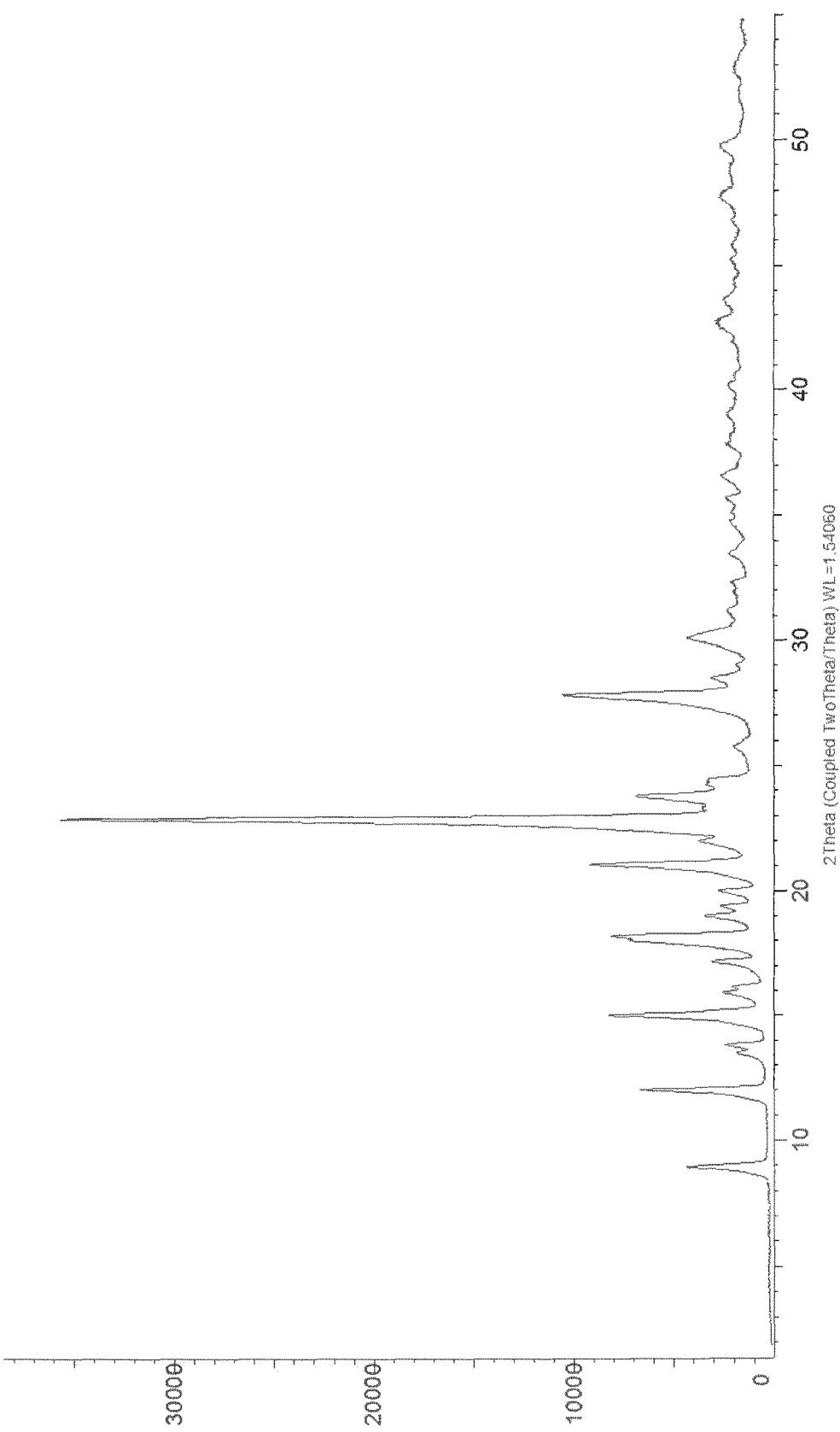
FIG. 2 shows the XRPD diffractogram of ibrutinib:benzoic acid co-crystal (1:1).

X-Ray Powder Diffraction (XRPD)
The product was characterized by means of x-ray powder diffraction. It is shown in the FIG. 2.

| | most characteristic peaks [°2θ] ± 0.2 °2θ | |
|---|---|---|
| sample | Primary characterising peaks | Secondary characterising peaks |
| ibrutinib:benzoic acid (1:1) | 9.1  12.1  13.7  13.9  23.0 | 16.1  16.2  19.1  20.1  21.2 |

The complete list of XRPD diffraction peaks of ibrutinib benzoic acid co-crystal (1:1):

| Angle ° (2Θ) | Relative Intensity % |
|---|---|
| 9.1 | 12.5% |
| 12.1 | 17.9% |
| 13.7 | 3.9% |
| 13.9 | 5.3% |
| 15.1 | 23.9% |
| 16.1 | 5.9% |
| 16.2 | 3.6% |
| 17.3 | 7.1% |
| 18.2 | 19.8% |
| 19.1 | 7.7% |
| 19.5 | 4.5% |
| 20.1 | 4.7% |
| 21.2 | 24.0% |
| 22.1 | 7.9% |
| 23.0 | 100.0% |
| 23.9 | 17.7% |
| 24.4 | 6.5% |
| 25.8 | 2.3% |
| 27.9 | 27.6% |
| 28.6 | 5.2% |
| 29.1 | 1.3% |
| 30.3 | 8.9% |
| 31.3 | 2.5% |
| 32.5 | 2.3% |
| 33.6 | 2.4% |
| 34.9 | 2.0% |
| 35.3 | 1.8% |
| 35.8 | 2.6% |
| 36.7 | 3.1% |
| 38.0 | 2.1% |
| 39.2 | 1.7% |
| 40.2 | 1.7% |
| 42.8 | 3.5% |
| 43.8 | 2.2% |
| 45.3 | 1.2% |
| 45.9 | 1.1% |
| 46.9 | 1.2% |
| 47.9 | 2.7% |
| 49.9 | 2.8% |

Figure 3:
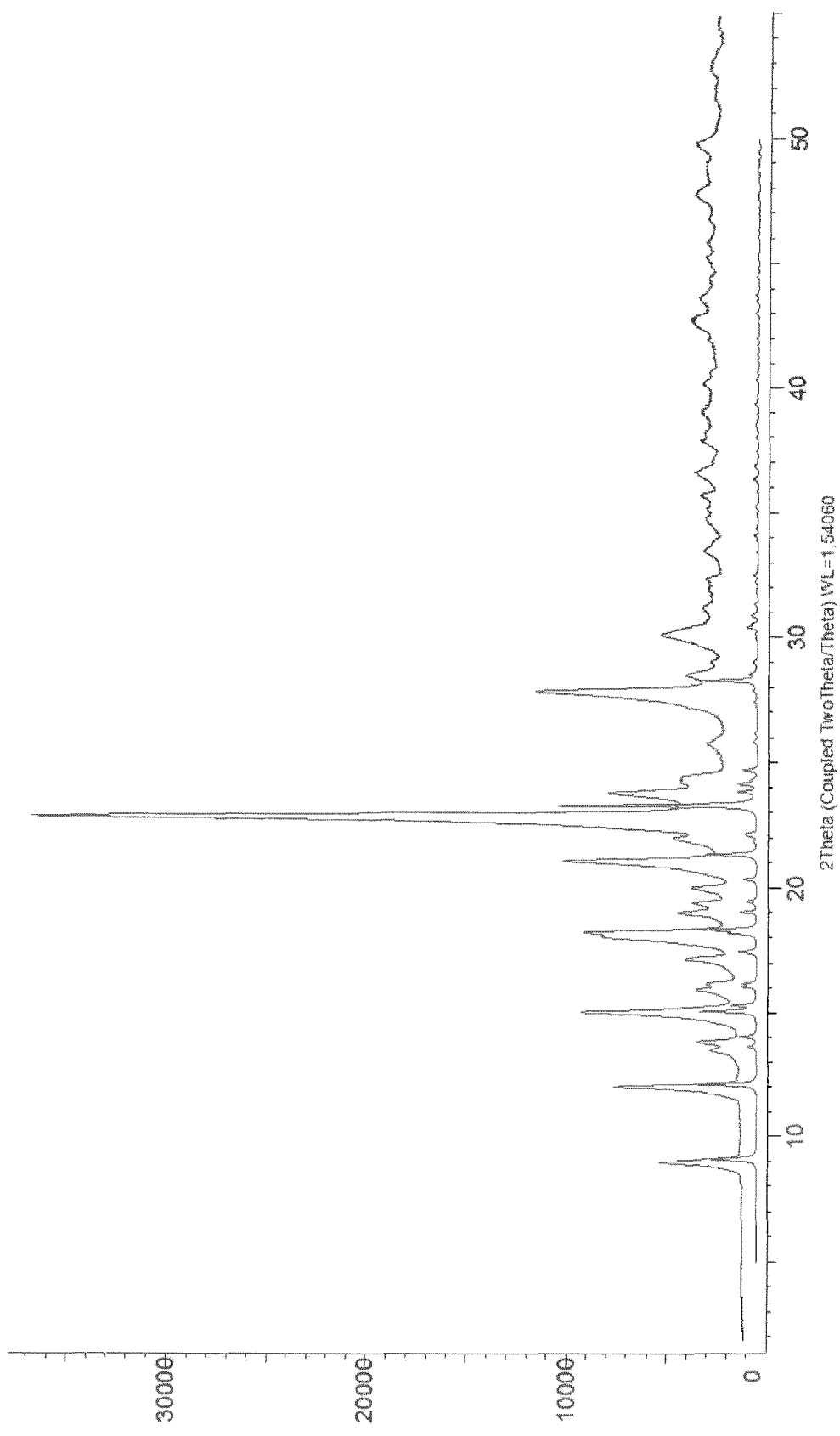
FIG. 3 shows an XRPD diffractogramm of ibrutinib:benzoic acid co-crystal (1:1) (at the top) compared with a simulated powder diffractogram produced from the atomic positions resulting from the three-dimensional x-ray structure of ibrutinib:benzoic acid co-crystal (1:1).

Also a comparative of this diffractogram with the simulated powder pattern from the single-crystal study results is shown in FIG. 3.

UHPLC/UV

Figure 4:
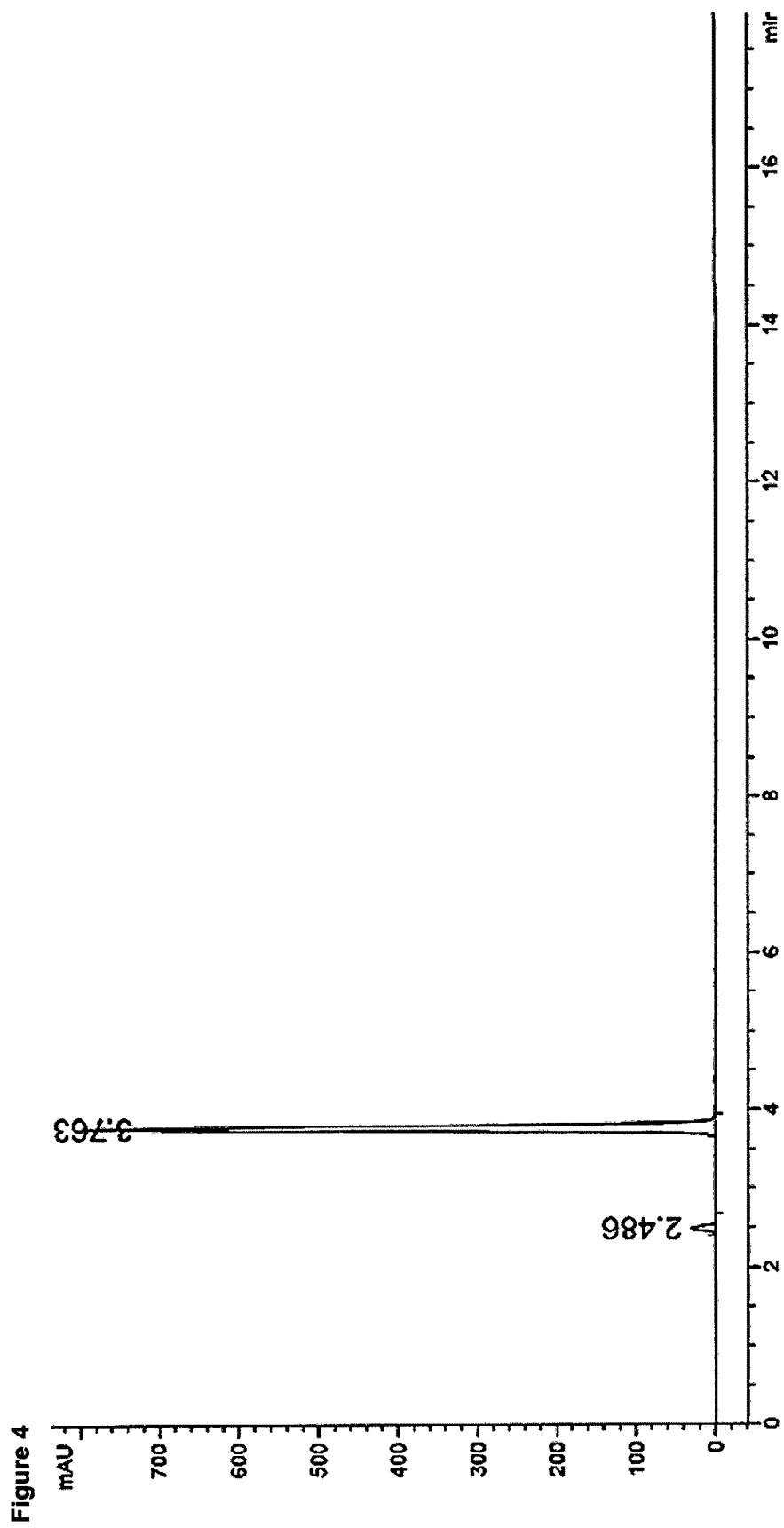
FIG. 4 shows an UHPLC/UV analysis of ibrutinib:benzoic acid (1:1) co-crystal. Signal at Rt=2.49 min corresponds to benzoic acid.

The chromatogram from UHPLC/UV analysis is shown in FIG. 4. No impurities were detected (Rt=2.486 min: benzoic acid; Rt=3.763 min: ibrutinib).

Storage Stability of Ibrutinib: Benzoic Acid

One batch of the ibrutinib:benzoic acid cocrystal (stability batch) was stored in open and closed containers in a climate chamber at 40° C./75% relative humidity ("accelerated conditions"). After storage for 4, 8 and 12 weeks, samples were analyzed by UHPLC/UV (chemical purity) as well as by XRPD (solid state stability). The results of UHPLC/UV analysis, summarized in the following table demonstrate that the chemical purity of the ibrutinib:benzoic acid cocrystal remained unchanged.

| Conditions (40° C./75% RH) | Open | Close |
|---|---|---|
| 4 Weeks | 99.74% | 99.90% |
| 8 Weeks | 99.77% | 99.90% |
| 12 Weeks | 99.80% | 99.91% |

The results of XRPD analysis confirmed that the solid state of the ibrutinib:benzoic acid cocrystal remained unchanged during storage under accelaerated conditions.

X-Ray Single Crystal Study of Ibrutinib:Benzoic Acid Co-Crystal (1:1)

The absolute configuration of the determined molecular structure matched the expected configuration, the Flack parameter was refined to a value of 0.04 (13), thus it corroborates the assignment. Hydrogen atoms were refined according to a riding model with exception of heteroatom-bonded hydrogen atoms whose positions were refined without restraints.

| | |
|---|---|
| Empirical formula | $C_{32}H_{30}N_6O_4$ |
| Formula weight | 562.63 |
| Temperature | 180 K |
| Wavelength | 1.54180 Å |
| Crystal system | triclinic |
| Space group | P1 |
| Unit cell dimensions | |
| a [Å] | 7.3974(2) |
| b [Å] | 9.7644(2) |
| c [Å] | 9.9369(2) |
| α [°] | 82.965(2) |
| β [°] | 81.427(2) |
| γ [°] | 88.055(2) |
| Volume [Å$^3$] | 704.30(1) |
| Z | 1 |
| Density (calculated) [g · cm$^{-3}$] | 1.326 |
| Absorption coefficient [mm$^{-1}$] | 0.731 |
| F(000) | 296 |
| Crystal size [mm] | 0.72 × 0.47 × 0.38 |
| Theta range for data collection | 4.53 to 77.22 |
| Index ranges | $-9 \leq h \leq 9, -12 \leq k \leq 12, -12 \leq l \leq 12$ |
| Reflections collected | 22735 |
| Independent reflections | 5472 (0.047) |
| [R(int)] | |
| Completeness to Theta = 77.22° | 97.8% |
| Absorption correction | Semi-empirical from equivalents |
| Max. and min. transmission | 0.76 and 0.20 |
| Refinement method | Full-matrix least-squares on F$^2$ |
| Data/parameters/restraints | 5467/390/8 |
| Goodness-of-fit on F$^2$ | 0.9338 |
| Final R indices [I > 2σ(I)] | $R_1 = 0.0343, wR_2 = 0.0922$ |
| Flack parameter | 0.04(13) |
| Final R indices [all data] | $R_1 = 0.0351, wR_2 = 0.0944$ |
| Largest diff. peak and hole [e · Å$^{-3}$] | 0.18 and −0.15 |

Figure 5:
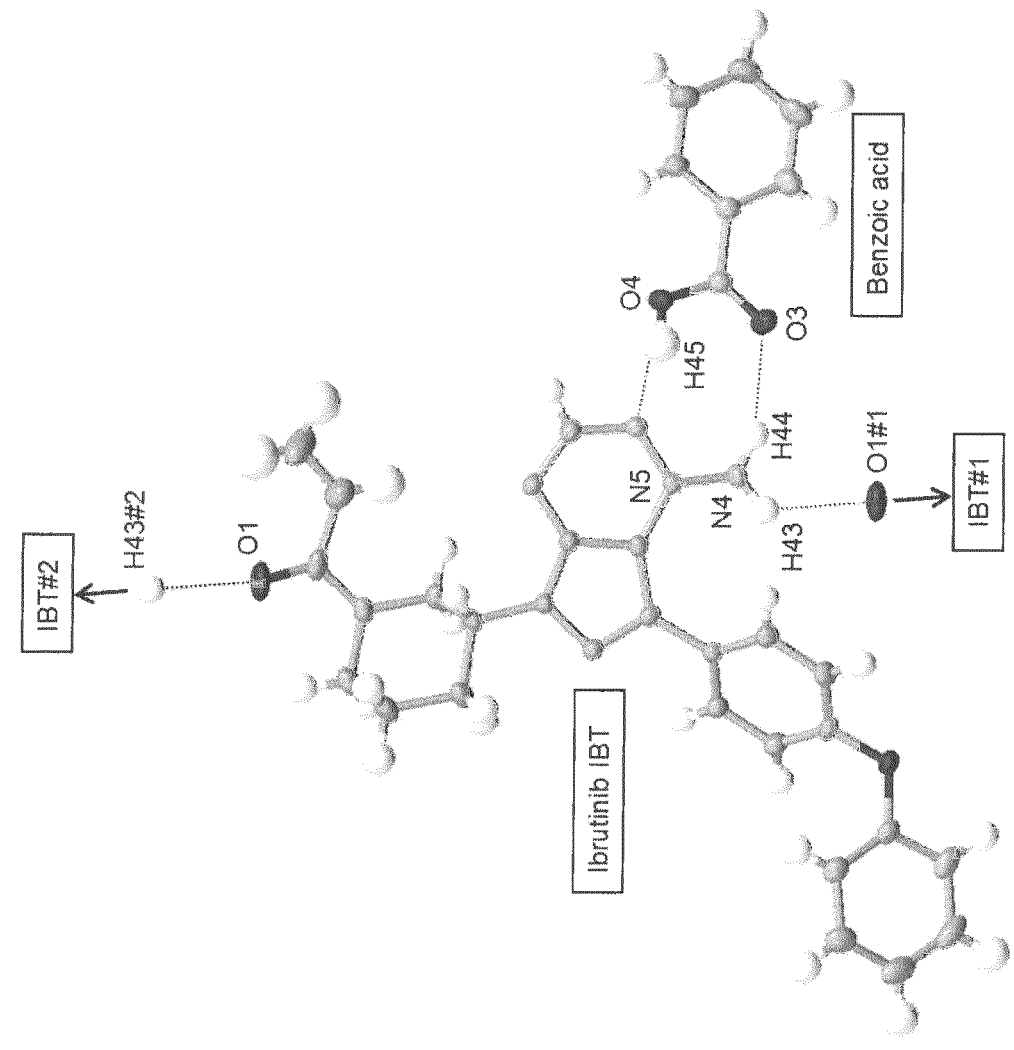
FIG. 5 shows the position of benzoic acid bound through hydrogen bonds to ibrutinib base as observed in the three-dimension crystal structure analysis of a single crystal on ibrutinib:benzoic acid co-crystal (1:1).

As is shown in FIG. 5, the packing of ibrutinib:benzoic acid co-crystal, consist in 1 molecule of ibrutinib and 1 molecule of Benzoic acid, i.e. a molar ratio of 1:1 with a triclinic symmetry.

There are three hydrogen bonds in the structure.

Firstly, the H-bond between ibrutinib and benzoic acid (O4-H45···N5) what confirms that the new solid state is a co-crystal, instead of a benzoate salt of ibrutinib. If the carboxyl group were deprotonated, the electrons would delocalize, causing almost same length of both C—O bonds (C26-O3 and C26-O4 in FIG. 5b). In this case, it is clear that the carboxyl group is protonized, as there is a distance C=O of 1.219 (2) Å (C26-O3) and C—O—H, with C—O 1.313 (2) Å (C26-O4). The carboxyl proton was located in difference Fourier map and its position was refined without restraints.

Secondly, H-bond between ibrutinib and benzoic acid (N4-H···O3) is a soft-moderate H-bond which makes stronger the union between ibrutinib and the co-former.

And finally, there is a H-bond between the amine group of ibrutinib and the carbonyl group of the next ibrutinib molecule.

The calculated atom distances and the angle of the H-bonds:

|  | D—H ... A | D—H (Å) | H ... A (Å) | D ... A (Å) | D—H ... A(°) |
|---|---|---|---|---|---|
| H-bond 1 | O4—H45 ... N5 | 0.97(3) | 1.64 | 2.582(2) | 163(3) |
| H-bond 2 | N4—H44 ... O3 | 0.94 | 2.26 | 3.164(2) | 161(2) |
| H-bond 3 | N4—H43 ... O1 | 0.92(2) | 2.19 | 2.846(2) | 127(2) |

Example 2: Preparation of Ibrutinib:Fumaric Acid Co-Crystal (2:1)

Experiment 1:

3 g (6.8 mmol) ibrutinib form A was suspended together with 0.8 g (6.8 mmol) fumaric acid in 27 mL MeOH at room temperature (RT). The suspension was heated to 70° C. A clear solution was obtained. The solution was let slowly cooled down to RT while a white solid started to precipitate. The precipitate was isolated by filtration and dried at 40° C./10 mbar for 72 hours (Yield: 70%).

The sample was analysed by means of XRPD and $^1$H-NMR spectroscopy.

Experiment 2:

Analogous to the Experiment 1, the procedure was performed with 800 mg (1.8 mmol) ibrutinib form A and 210 mg (1.8 mmol) fumaric acid with a 43% yield.

The sample was analysed by means of XRPD and $^1$H-NMR spectroscopy.

Experiment 3:

1 L reactor was charged with ibrutinib (50 g), fumaric acid (26.35 g) and methanol (350 mL), the mixture was heated to 68° C. until dissolution. The solution was cooled to 45° C. during 1 hour and seeded with ibrutinib:fumaric acid co-crystals. The mixture was cooled to 35° C. during 1 hour and stirred at 35° C. for 2 hours until precipitate was obtained. The slurry was cooled to 0° C. during 6 hours and stirred at 0° C. overnight.

The slurry was filtered under vacuum, washed with cooled methanol (100 mL) and dried at 50° C. over 72 hours in vacuum to give 49.46 g of white solid (Yield: 87.5%).

The results of Experiments 1 to 3:

$^1$H-NMR Spectroscopy

The sample was analyzed in a 400 MHz-NMR spectrometer. As solvent, DMSO-d$_6$ was used. The $^1$H-NMR spectrum is shown in FIG. 5. The signals are summarized below (*=signals of fumaric acid):

1.57 (br. s., 1H); 1.75-2.01 (m, 1H); 2.11 (br. s., 1H); 2.18-2.46 (m, 1H); 2.65 (s, 1H); 3.01 (d, J=9.78 Hz, 1H); 3.20 (br. s., 1H); 3.68 (br. s., 1H); 4.06 (d, J=12.12 Hz, 1H); 4.19 (br. s., 1H); 4.52 (br. s., 1H); 4.69 (br. s., 1H); 5.57 (d, J=10.17 Hz, 1H); 5.69 (d, J=11.34 Hz, 1H); 5.99-6.19 (m, 1H); 6.52-6.63 (m, 1H*); 6.64-6.77 (m, 1H); 6.78-6.98 (m, 1H); 7.09-7.19 (m, 4H); 7.31-7.53 (m, 2H); 7.64 (d, J=7.82 Hz, 2H); 8.24 (s, 1H); 13.10 (br. s., 1H*).

The integration values of the 1.93 ppm signal (1H) of ibrutinib and the 6.60 ppm signal (2H) from fumaric acid were 1 and 1 resp. It corresponds with a ibrutinib:fumaric acid=2:1 molar ratio.

X-Ray Powder Diffraction (XRPD)

Figure 6:
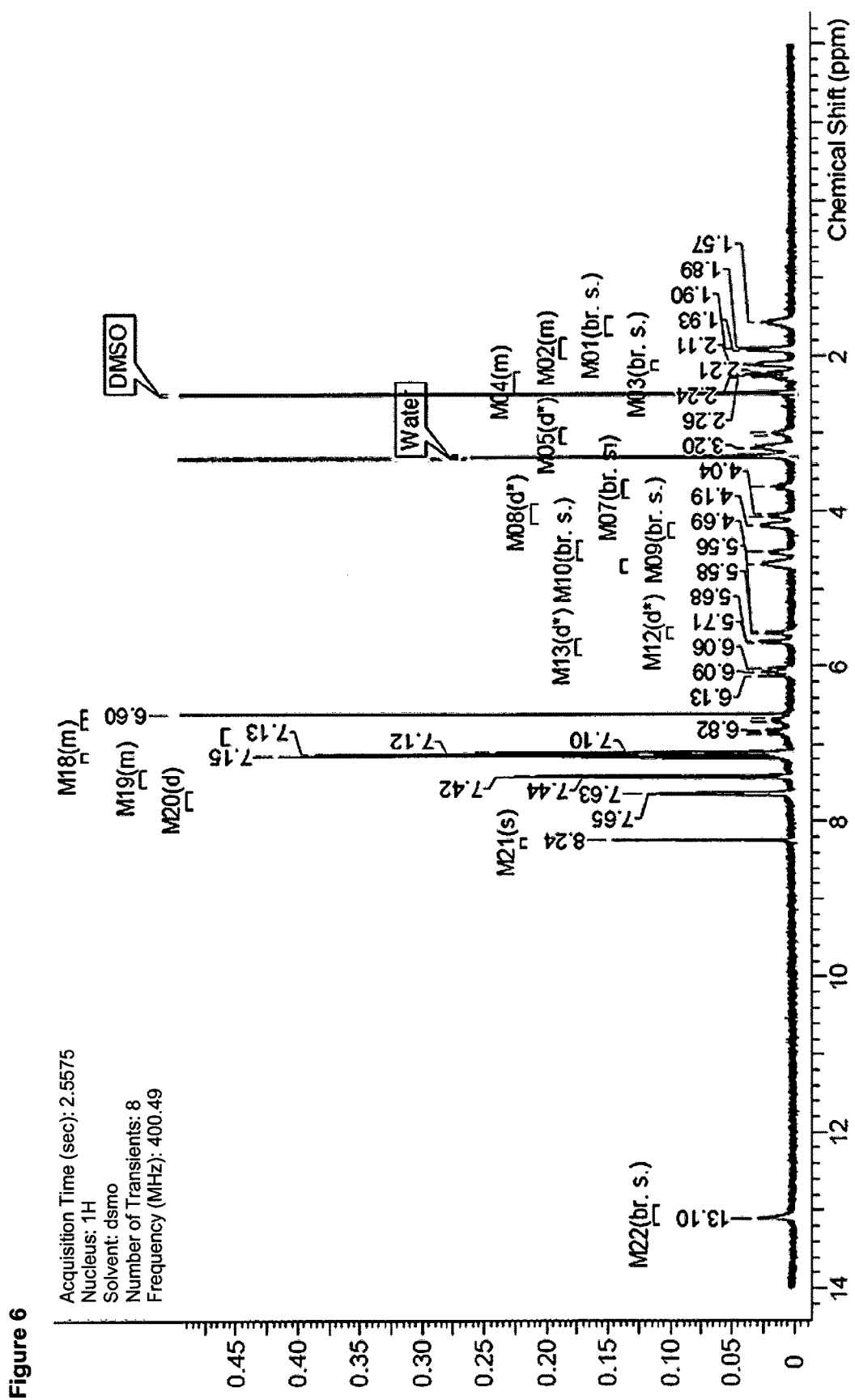
FIG. 6 shows the $^1$H-NMR spectrum of ibrutinib:fumaric acid co-crystal (2:1) ($^1$H-NMR in DMSO-$d_6$, 400 MHz).
Figure 7:
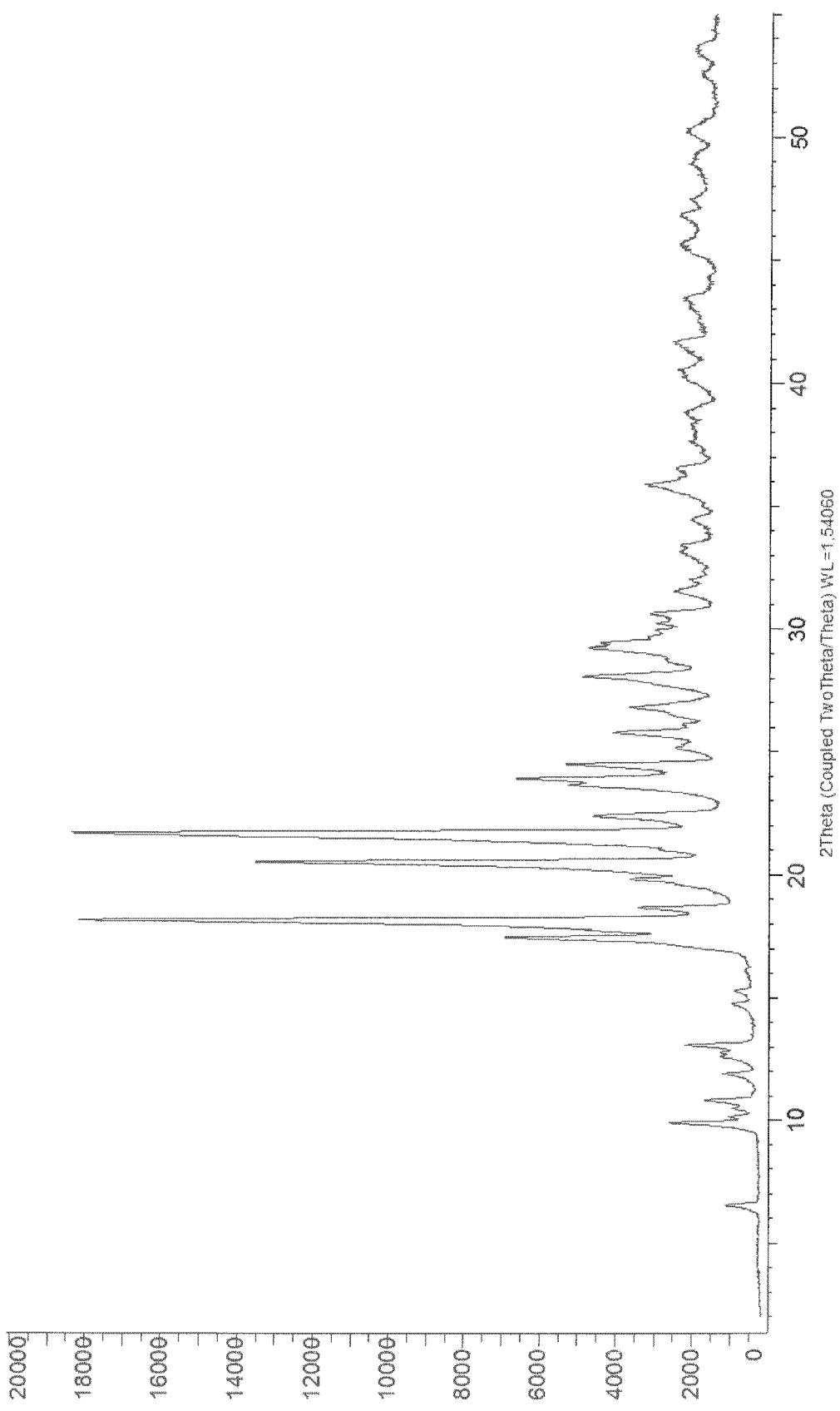
FIG. 7 shows the XRPD diffractogram of ibrutinib:fumaric acid co-crystal (2:1).

The product was characterized by means of x-ray powder diffraction. It is shown in the FIG. 6.

The x-ray powder diffractogram of ibrutinib:fumaric acid co-crystal is characterized by the following signals:

| sample | most characteristic peaks [°2θ] ± 0.2 °2θ | | | | | | | | | |
|---|---|---|---|---|---|---|---|---|---|---|
|  | Primary characterising peaks | | | | | Secondary characterising peaks | | | | |
| ibrutinib:Fumaric acid | 9.9 | 17.4 | 18.7 | 20.5 | 21.7 | 6.5 | 13.0 | 18.2 | 22.4 | 23.9 |

The complete list of XRPD diffraction peaks of ibrutinib fumaric acid co-crystal (2:1):

| Angle ° (2Θ) | Relative Intensity % |
|---|---|
| 6.5 | 3.8% |
| 9.9 | 14.0% |
| 10.1 | 4.3% |
| 10.5 | 3.1% |
| 10.8 | 6.8% |
| 11.9 | 5.4% |
| 12.6 | 4.6% |
| 12.8 | 4.4% |
| 13.0 | 6.9% |
| 14.7 | 2.7% |
| 15.2 | 2.2% |
| 17.4 | 32.8% |
| 18.2 | 100.0% |

| Angle ° (2Θ) | Relative Intensity % |
|---|---|
| 18.7 | 14.6% |
| 19.8 | 15.0% |
| 20.5 | 72.4% |
| 21.0 | 8.5% |
| 21.7 | 95.9% |
| 22.4 | 17.6% |
| 23.6 | 20.2% |
| 23.9 | 29.5% |
| 24.4 | 18.4% |
| 25.2 | 4.4% |
| 25.7 | 13.7% |
| 26.8 | 12.4% |
| 28.1 | 17.7% |
| 29.3 | 15.4% |
| 30.6 | 8.3% |
| 31.5 | 5.4% |
| 32.0 | 2.9% |
| 33.1 | 3.7% |
| 33.4 | 4.7% |
| 34.4 | 2.3% |
| 35.8 | 8.8% |
| 36.5 | 4.6% |
| 38.8 | 3.7% |
| 40.4 | 3.9% |
| 41.6 | 5.4% |
| 43.4 | 4.1% |
| 45.6 | 4.4% |
| 46.8 | 4.6% |
| 49.1 | 2.5% |
| 50.2 | 3.6% |
| 52.6 | 1.7% |
| 53.5 | 3.3% |

UHPLC/UV

Figure 8:
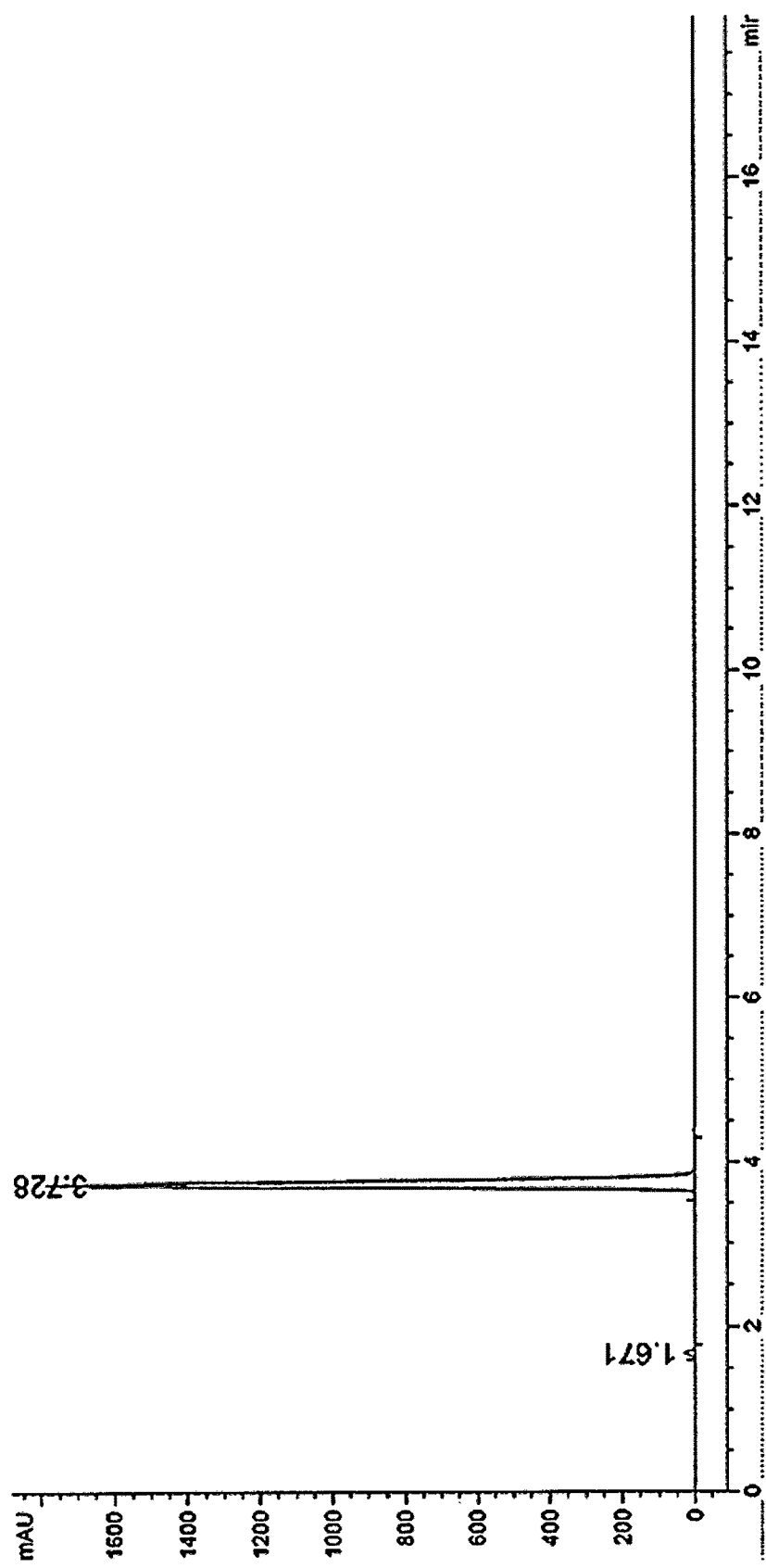
FIG. 8 shows an UHPLC/UV analysis of ibrutinib:fumaric acid (2:1) co-crystal. Signal at Rt=1.67 min corresponds to fumaric acid.

The chromatogram from UHPLC/UV analysis is shown in FIG. 8. No impurities were detected (Rt=1.671 min: fumaric acid, Rt=3.728 min: ibrutinib).

Storage Stability of Ibrutinib:Fumaric Acid

One batch of the ibrutinib:fumaric acid cocrystal (stability batch) was stored in open and closed containers under accelerated conditions. After storage for 4, 8 and 12 weeks, samples were analyzed by UHPLC/UV (chemical purity) as well as by XRPD (solid state stability). The results of UHPLC/UV analysis, summarized in the following table demonstrate that the chemical purity of the ibrutinib:fumaric acid cocrystal remained unchanged.

| Conditions (40° C./75% RH) | Open | Close |
|---|---|---|
| 4 Weeks | 99.85% | 99.93% |
| 8 Weeks | 99.91% | 99.93% |
| 12 Weeks | 99.83% | 99.90% |

The results of XRPD analysis confirmed that the solid state of the ibrutinib:fumaric acid cocrystal remained unchanged during storage under accelaerated conditions.

X-Ray Single Crystal Study of Ibrutinib:Fumaric Acid Co-Crystal (2:1)

| | |
|---|---|
| Temperature | 180 K |
| Wavelength | 1.54178 Å |
| Crystal system | triclinic |
| Space group | P1 |
| Unit cell dimensions | |
| a [Å] | 9.8994 (5) |
| b [Å] | 9.9979 (5) |
| c [Å] | 13.9063 (7) |
| α [°] | 93.268 (2) |
| β [°] | 99.856 (2) |
| Y [°] | 115.655 (2) |
| Volume [Å³] | 1208.96 (6) |

Figure 9:
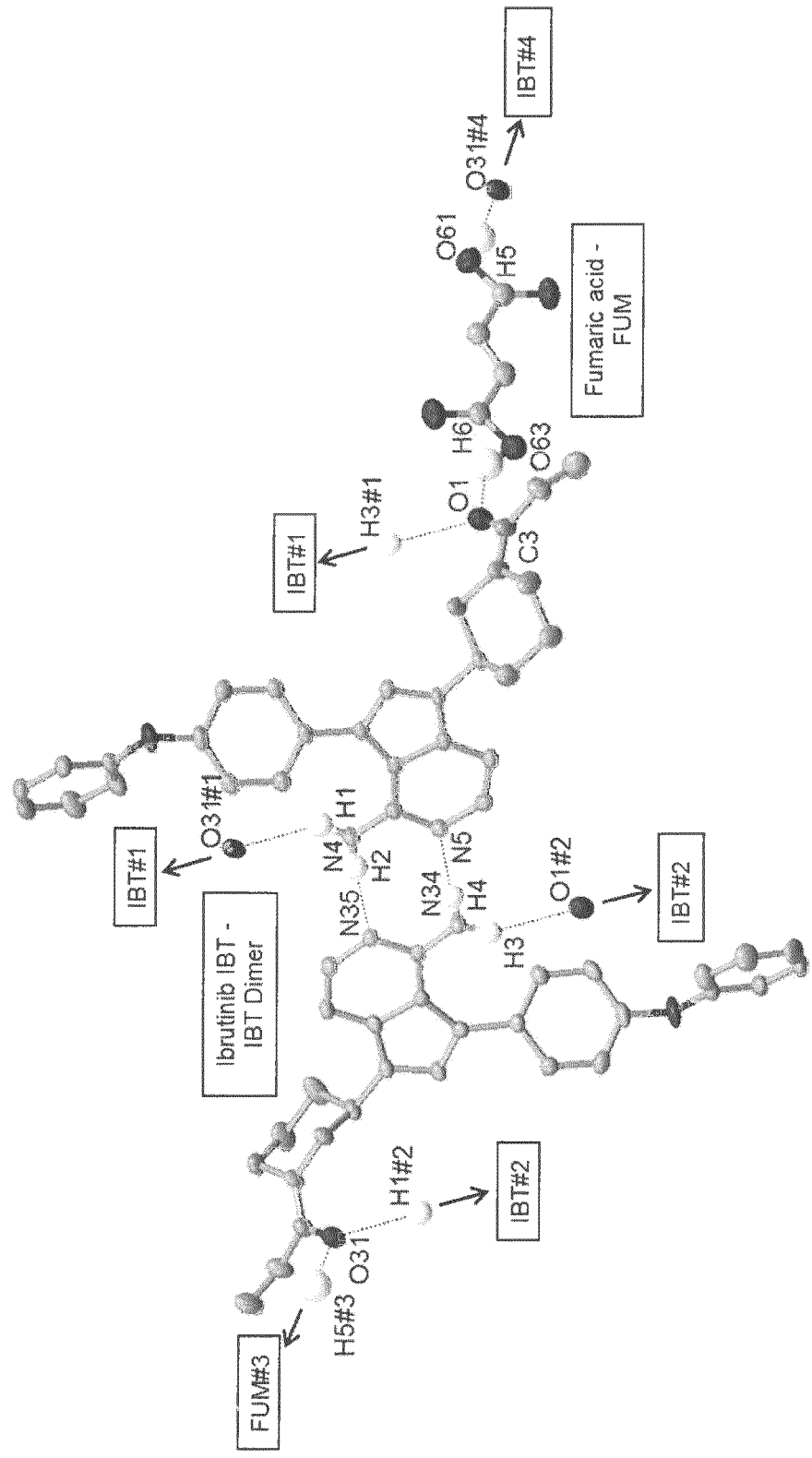
FIG. 9 shows the position of fumaric acid bound through hydrogen bonds to ibrutinib base as observed in the three-dimension crystal structure analysis of a single crystal on ibrutinib:fumaric acid co-crystal (2:1).

As is shown in FIG. 9, the packing of ibrutinib:fumaric acid cocrystal consists of two molecules of ibrutinib in dimeric formation and one molecule of fumaric acid, i.e. a molar ratio of 2:1 with a triclinic symmetry. The dimer is formed through hydrogen bonds between N4-H2 and N35 and N34-H4 and N5 of the respective ibrutinib molecules. The amide group of ibrutinib establishes H-bonds with the acid group of fumaric acid (both carboxylic groups of fumaric acid are connected with H-bonds to ibrutinib: O61-H5 to O31 and O63-H6 to O6 of the respective molecules. Moreover, the ibrutinib dimer is bonded to the next dimer in the crystal lattice with two H-bonds per molecule: N4-H1 to O31 and N34-H3 to O1. The geometry of fumaric acid clearly shows distances typical for C=O and C—OH, which are C61-O61 1.329 (3) Å, C61-O62 1.197 (3) Å, C64-O63 1.312 (3) Å and C64-O64 1.207 (3) Å.

If the fumaric acid is deprotonated, the distances of C—O would be approximately the same distance, reflecting the electron resonance of the possible anion.

The calculated atom distances and angles of the H-bonds are the following:

| | D—H...A | D—H (Å) | H...A (Å) | D...A (Å) | D—H...A(°) |
|---|---|---|---|---|---|
| H-bond 1 | N4—H2...N35 | 0.899 | 2.159 | 3.056(5) | 175.28(7) |
| H-bond 2 | N34—H4...N5 | 0.887 | 2.000 | 2.885(5) | 175.89(8) |
| H-bond 3 | O61—H5...O31 | 0.897 | 1.818 | 2.714(5) | 178.22(9) |
| H-bond 4 | O63—H6...O1 | 0.907 | 2.043 | 2.737(5) | 132.32(8) |
| H-bond 5 | N4—H1...O31 | 0.878 | 2.359 | 3.052(5) | 135.92(7) |
| H-bond 6 | N34—H3...O1 | 0.873 | 2.524 | 3.193(5) | 133.98(7) |

Stress-Testing of Ibrutinib Co-Crystal with Fumaric Acid

A sample of the Ibrutinib-fumaric acid co-crystal was tested for its polymorphic stability to extreme conditions. The following conditions were applied to small samples (about 0.1 g each) of the powdery co-crystal:

1. 1 minute of 3 tons pressure, using T25 ATLAS power press (by Specac).
2. About 1 minute of strong grinding using pestle and mortar.
3. About 1 minute of strong grinding using pestle and mortar after adding one drop of water to the powder.

4. About 1 minute of strong grinding using pestle and mortar after adding one drop of ethanol to the powder.
5. About 1 minute of strong grinding using pestle and mortar after adding one drop of isopropanol to the powder.
6. Heating to 100° C. for 30 minutes.
7. 1 week storage under 100% relative humidity at room temperature.

Figure 14:
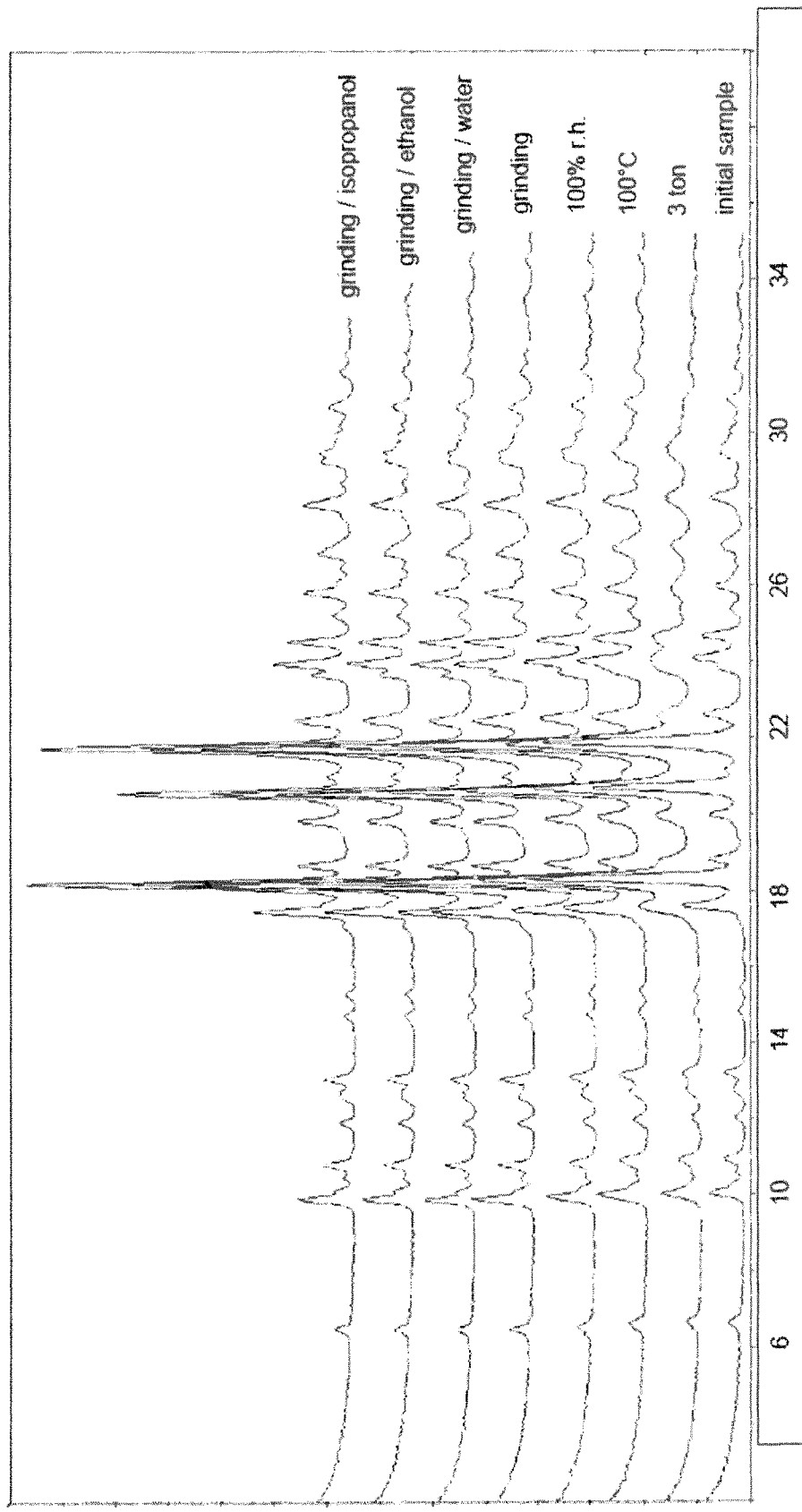
FIG. 14 shows the XRPD diffractogram of ibrutinib:fumaric co-crystal after stress testing.

All the samples were tested in XRPD after the stress-tests. No change was observed in the XRPD pattern, as shown in FIG. 14.

Example 3: Preparation of Ibrutinib:Succinic Acid Co-Crystal

Experiment 1:

143 mg (0.32 mmol) ibrutinib was suspended together with 156 mg (1.32 mmol) succinic acid in 1 mL MeOH at room temperature (RT). A clear solution was obtained after 5 minutes of stirring. After 60 minutes a white solid started to precipitate. The solution was let overnight with stirring at RT for the complete precipitation. The precipitate was isolated by filtration (Yield: 21%).

The sample was analysed by means of XRPD and $^1$H-NMR spectroscopy.

Experiment 2:

1 g (2.3 mmol) ibrutinib was suspended together with 1 g (8.5 mmol) succinic acid in 7 mL MeOH at room temperature (RT). A clear solution was obtained after 15 minutes of stirring. After 60 minutes, a white solid started to precipitate. The solution was let over the weekend with stirring at RT for the complete precipitation. The precipitate was isolated by filtration (Yield: 67%).

The sample was analysed by means of XRPD and $^1$H-NMR spectroscopy.

The results of Experiments 1 to 2:

$^1$H-NMR Spectroscopy

Figure 10:
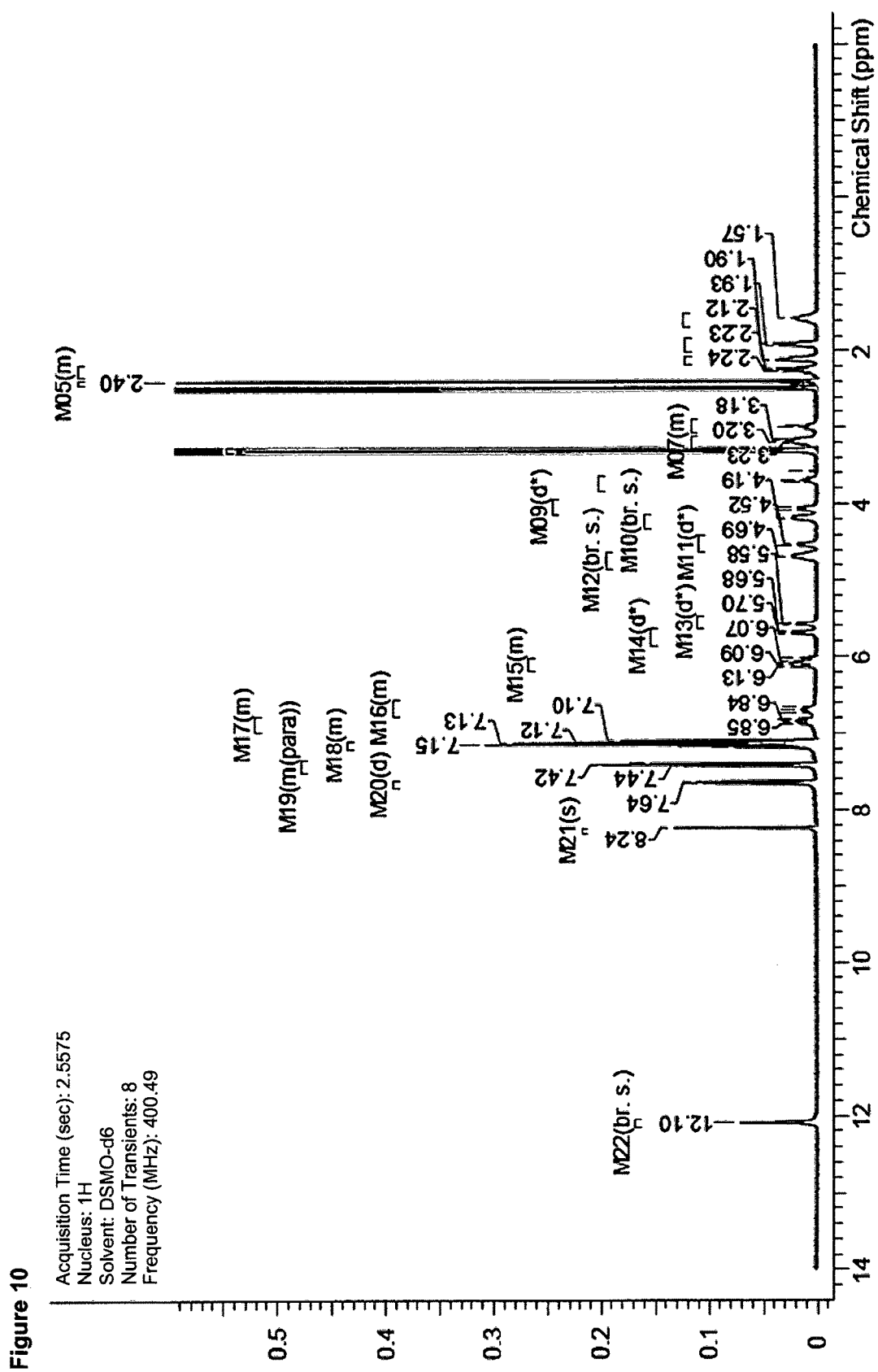
FIG. 10 shows the $^1$H-NMR spectrum of ibrutinib:succinic co-crystal ($^1$H-NMR in DMSO-$d_6$, 400 MHz).

The sample was analyzed in a 400 MHz-NMR spectrometer. As solvent, DMSO-$d_6$ was used. The $^1$H-NMR spectrum is shown in FIG. 10. The signals are summarized below (*=signals of succinic acid):

1.57 (br. s., 1H); 1.92 (d, J=13.69 Hz, 1H); 2.12 (br. s., 1H); 2.18-2.32 (m, 1H); 2.38-2.42 (m, 3H*); 2.88-3.07 (m, 1H); 3.10-3.27 (m, 1H); 3.70 (d, J=10.56 Hz, 1H); 4.06 (d, J=13.29 Hz, 1H); 4.19 (br. s., 1H); 4.54 (d, J=12.12 Hz, 1H); 4.69 (br. s., 1H); 5.57 (d, J=9.78 Hz, 1H); 5.69 (d, J=10.56 Hz, 1H); 6.00-6.18 (m, 1H); 6.54-6.77 (m, 1H); 6.77-6.98 (m, 1H); 7.09-7.20 (m, 5H); 7.33-7.51 (m, 2H); 7.65 (d, J=7.82 Hz, 2H); 8.24 (s, 1H); 12.10 (br. s., 1H*).

The integration values of the 1.92 ppm signal (1H) of ibrutinib and the 2.40 ppm signal (4H) from succinic acid were 1 and 2.5 resp.

X-Ray Powder Diffraction (XRPD)

Figure 11:
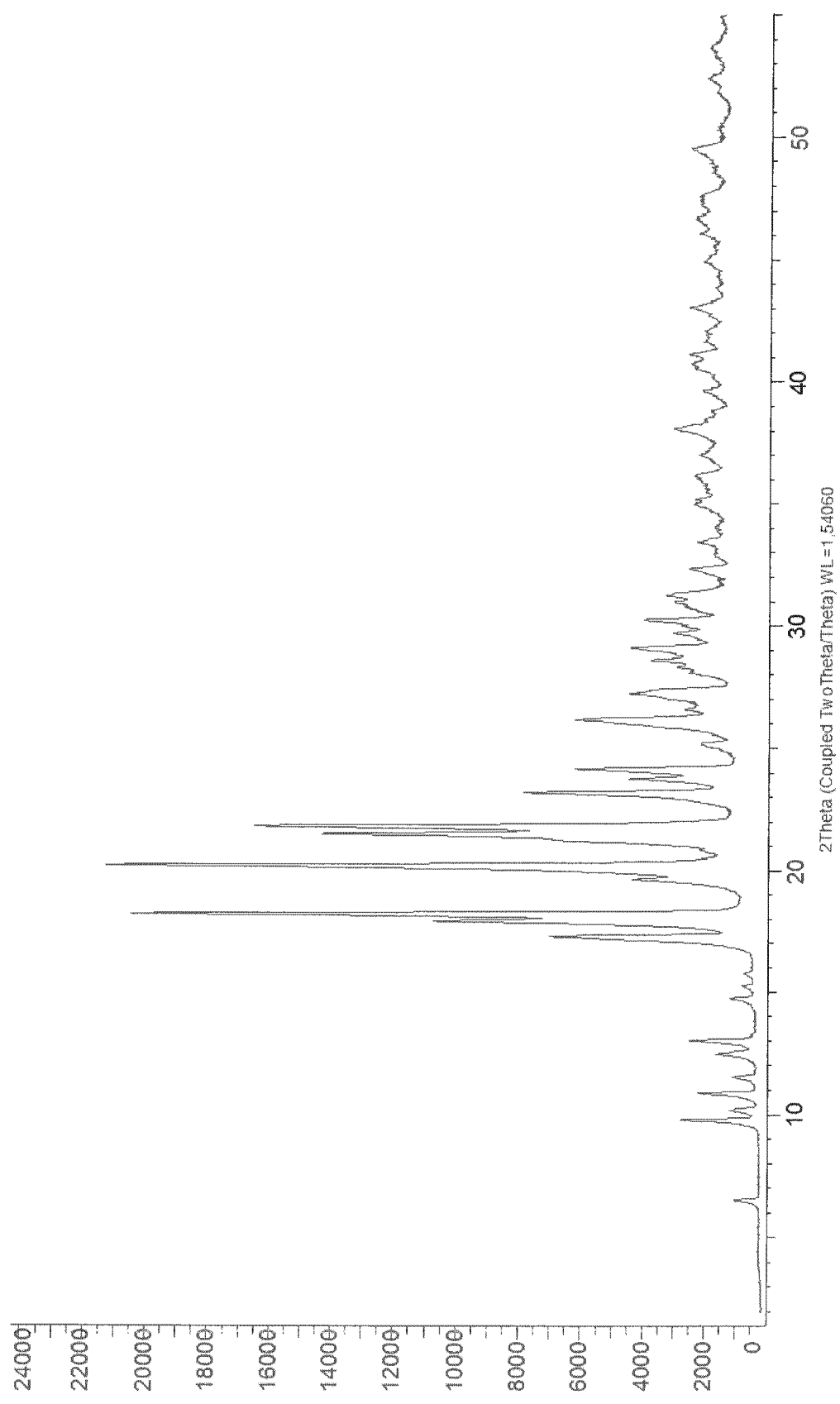
FIG. 11 shows the XRPD diffractogram of ibrutinib:succinic acid co-crystal.

The product was characterized by means of x-ray powder diffraction. It is shown in the FIG. 11.

The x-ray powder diffractogram of ibrutinib:succinic acid cocrystal is characterized by the following signals:

| sample | most characteristic peaks [°2θ] ± 0.2 °2θ | |
|---|---|---|
| | Primary characterising peaks | Secondary characterising peaks |
| IBT:Succinic acid | 17.3  17.9  20.2  21.5  21.8 | 9.8  11.5  13.0  18.3  23.2 |

The complete list of XRPD diffraction peaks of ibrutinib:succinic acid co-crystal

| Angle ° (2Θ) | Relative Intensity % |
|---|---|
| 6.5 | 3.3% |
| 9.8 | 10.2% |
| 10.2 | 4.0% |
| 10.8 | 7.3% |
| 11.5 | 2.7% |
| 12.5 | 6.3% |
| 13.0 | 8.5% |
| 14.7 | 3.3% |
| 15.2 | 1.7% |
| 15.7 | 1.2% |
| 17.3 | 31.3% |
| 17.9 | 49.4% |
| 18.3 | 97.5% |
| 19.7 | 16.2% |
| 20.2 | 100.0% |
| 21.5 | 67.1% |
| 21.8 | 76.9% |
| 23.2 | 33.1% |
| 23.8 | 15.9% |
| 24.2 | 25.2% |
| 25.1 | 4.3% |
| 26.1 | 21.3% |
| 26.7 | 5.4% |
| 27.2 | 15.1% |
| 28.6 | 11.6% |
| 29.0 | 13.3% |
| 29.7 | 7.2% |
| 30.2 | 10.0% |
| 31.0 | 7.6% |
| 31.2 | 8.4% |
| 32.3 | 5.0% |
| 33.4 | 4.1% |
| 38.1 | 7.4% |
| 40.7 | 4.7% |
| 43.0 | 4.7% |
| 49.5 | 4.7% |

UHPLC/UV

Figure 12:
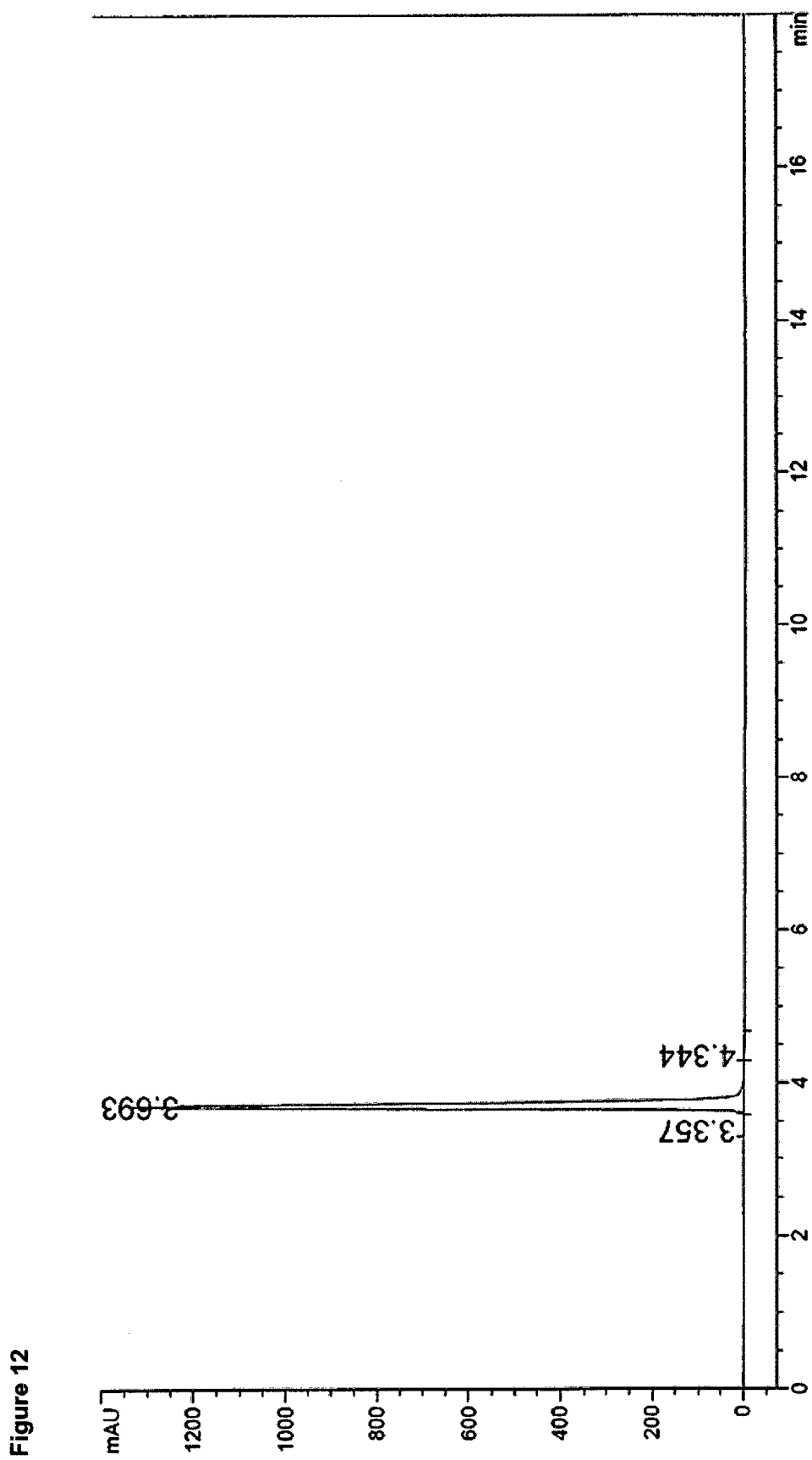
FIG. 12 shows an UHPLC/UV analysis of ibrutinib:succinic acid co-crystal.

The chromatogram from UHPLC/UV analysis is shown in FIG. 12 (Rt=3.693 min: ibrutinib; succinic acid not detected at this wavelength).

Storage Stability of Ibrutinib:Succinic Acid

One batch of the ibrutinib:succinic acid cocrystal (stability batch) was stored in open and closed containers under accelerated conditions. After storage for 4, 8 and 12 weeks, samples were analyzed by UHPLC/UV (chemical purity) as well as by XRPD (solid state stability). The results of UHPLC/UV analysis, summarized in the following table demonstrate that the chemical purity of the ibrutinib:succinic acid cocrystal remained unchanged.

| Conditions (40° C./75% RH) | Open | Close |
|---|---|---|
| 4 Weeks | 99.91 | 99.91 |
| 8 Weeks | 99.91 | 99.91 |
| 12 Weeks | 99.92 | 99.92 |

The results of XRPD analysis confirmed that the solid state of the ibrutinib:succinic acid cocrystal remained unchanged during storage under accelaerated conditions.

X-Ray Single Crystal Study of Ibrutinib:Succinic Acid Co-Crystal (2:1)

| Temperature | 180 K |
|---|---|
| Wavelength | 1.54178 Å |
| Crystal system | triclinic |
| Space group | P1 |
| Unit cell dimensions | |
| a [Å] | 10.0016 (3) |
| b [Å] | 13.8869 (4) |
| c [Å] | 18.0873 (5) |
| α [°] | 81.479 (1) |
| β [°] | 88.755 (1) |
| γ [°] | 79.974 (1) |
| Volume [Å$^3$] | 2446.48 (7) |

Figure 13:
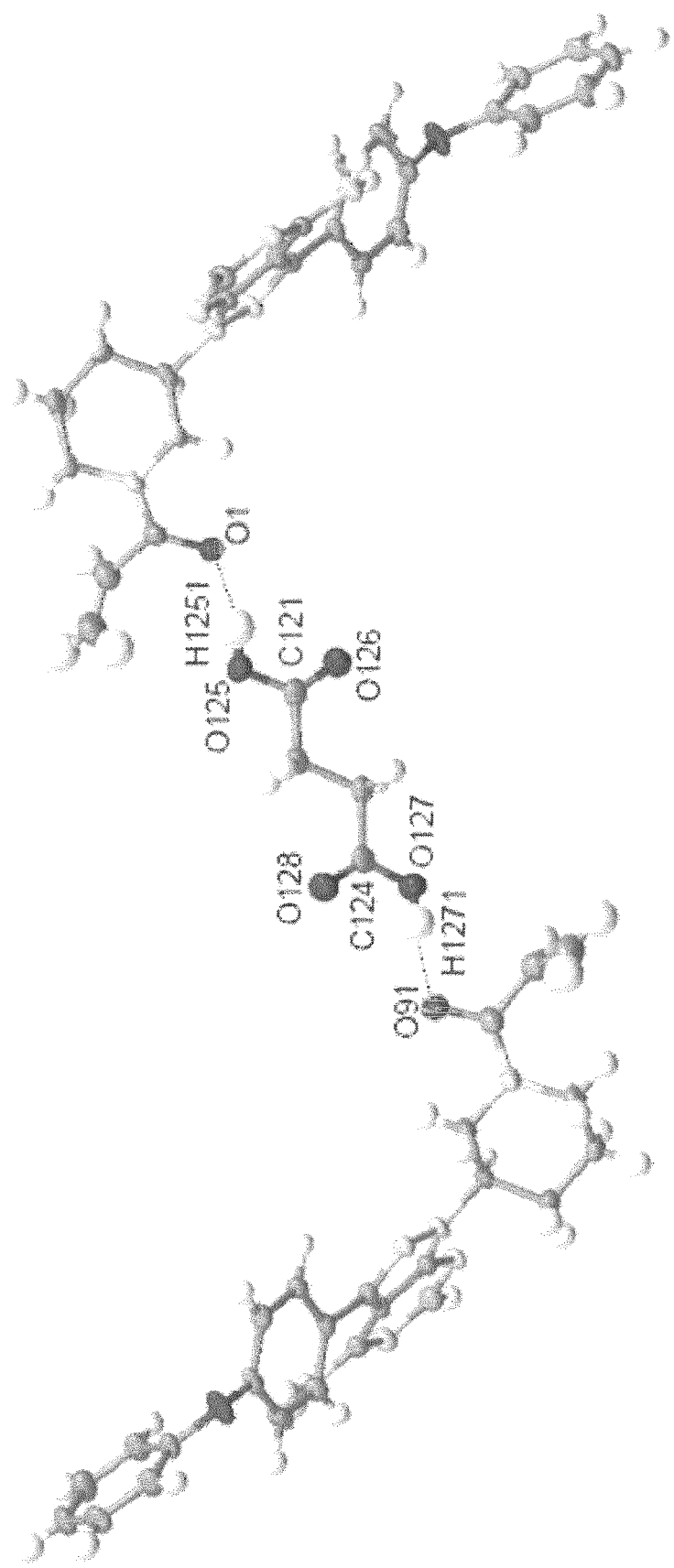
FIG. 13 shows the position of succinic acid bound through hydrogen bonds to ibrutinib base as observed in the three-dimensional crystal structure analysis of a single crystal on ibrutinib:succinic acid co-crystal (2:1).

The packing of ibrutinib:succinic acid cocrystal in one unit cell in a triclinic symmetry P1 consists of four molecules of ibrutinib and two molecules of succinic acid, i.e. a molar ratio of 2:1. The packing is stabilised by complex H-bond network of chains formed by Ibrutinib:succinic acid:ibrutinib unities. One of the two unities is shown in FIG. 13. The hydrogen atoms were found in relevant positions close to the succinic acid. The geometry of succinic acid clearly shows distances typical for C=O and C—OH, which are C124-O127 1.316 (4) Å, C124-O128 1.205 (4) Å, C121-O125 1.327 (3) Å and C121-O126 1.197 (4) Å.

If the succinic acid is deprotonated, the distances of C—O would be approximately the same distance, reflecting the electron resonance of the possible anion.

The calculated atom distances and angles of the H-bonds from the succinic acid to ibrutinib of the two unities in the unit cell are the following:

| | D—H...A | D—H (Å) | H...A (Å) | D...A (Å) | D—H...A(°) |
|---|---|---|---|---|---|
| H-bond 1 | O127—H1271...O91 | 0.823 | 1.894 | 2.7104) | 171.29(17) |
| H-bond 2 | O125—H1251...O1 | 0.892 | 1.838 | 2.714(4) | 166.69(16) |
| H-bond 1 | O137—H1371...O61 | 0.938 | 1.802 | 2.708(4) | 161.45(14) |
| H-bond 2 | O135—H1351...O31 | 1.050 | 1.700 | 2.706(4) | 159.00(16) |

Example 4:Pharmaceutical Formulations of Ibrutinib Co-Crystals

Experiment 1: Capsules

| Ibrutinib:benzoic acid co-crystal | 179 mg (corresponds to 140 mg free base) |
|---|---|
| Aerosil ® 200 (silicium dioxide) | 5 mg |
| Prosolv SMCC90 (silicified micro crystalline cellulose) | 197 mg |
| Ac-di-sol (croscramellose sodium) | 40 mg |
| Magnesium stearate | 3 mg |

Active ingredient and Aerosil were premixed, subsequently all other ingredients except magnesium stearate were blended in a free fall mixer for 15 min. Then, sieved magnesium stearate was added and the mixture was blended for further 5 min. The final blend was filled into capsules.

| Ibrutinib:fumaric acid co-crystal | 158.5 mg (corresponds to 140 mg free base) |
|---|---|
| Aerosil ® 200 (silicium dioxide) | 5 mg |
| Prosolv SMCC90 (silicified micro crystalline cellulose) | 197 mg |
| Ac-di-sol (croscramellose sodium) | 40 mg |
| Magnesium stearate | 3 mg |

Active ingredient and Aerosil were premixed, subsequently all other ingredients except magnesium stearate were blended in a free fall mixer for 15 min. Then, sieved magnesium stearate was added and the mixture was blended for further 5 min. The final blend was filled into capsules.

Experiment 2: Tablets

| Ibrutinib:benzoic acid co-crystal | 179 mg (corresponds to 140 mg free base) |
|---|---|
| Aerosil ® 200 (silicium dioxide) | 5 mg |
| Prosolv SMCC90 (silicified micro crystalline cellulose) | 197 mg |
| Ac-di-sol (croscramellose sodium) | 40 mg |
| Magnesium stearate | 5 mg |

Active ingredient and Aerosil were premixed, subsequently all other ingredients except magnesium stearate were blended in a free fall mixer for 15 min. Then, sieved magnesium stearate is added and the mixture was blended for further 5 min. The final blend was compressed into tablets.

| Ibrutinib:fumaric acid co-crystal | 158.5 mg (corresponds to 140 mg free base) |
|---|---|
| Aerosil ® 200 (silicium dioxide) | 5 mg |
| Prosolv SMCC90 (silicified micro crystalline cellulose) | 197 mg |
| Ac-di-sol (croscramellose sodium) | 40 mg |
| Magnesium stearate | 5 mg |

Active ingredient and Aerosil were premixed, subsequently all other ingredients except magnesium stearate were blended in a free fall mixer for 15 min. Then, sieved magnesium stearate was added and the mixture was blended for further 5 min. The final blend was compressed into tablets.

Comparative Example 1: Storage Stability of Ibrutinib Form E According to WO 2013/184572

Ibrutinib free base Form A (1 g) was suspended in toluene (12 mL) and the resulting slurry was stirred for 3.5 d at room temp. The product was filtered off and dried under reduced pressure for 22 h to provide Ibrutinib free base Form E.

Figure 15:
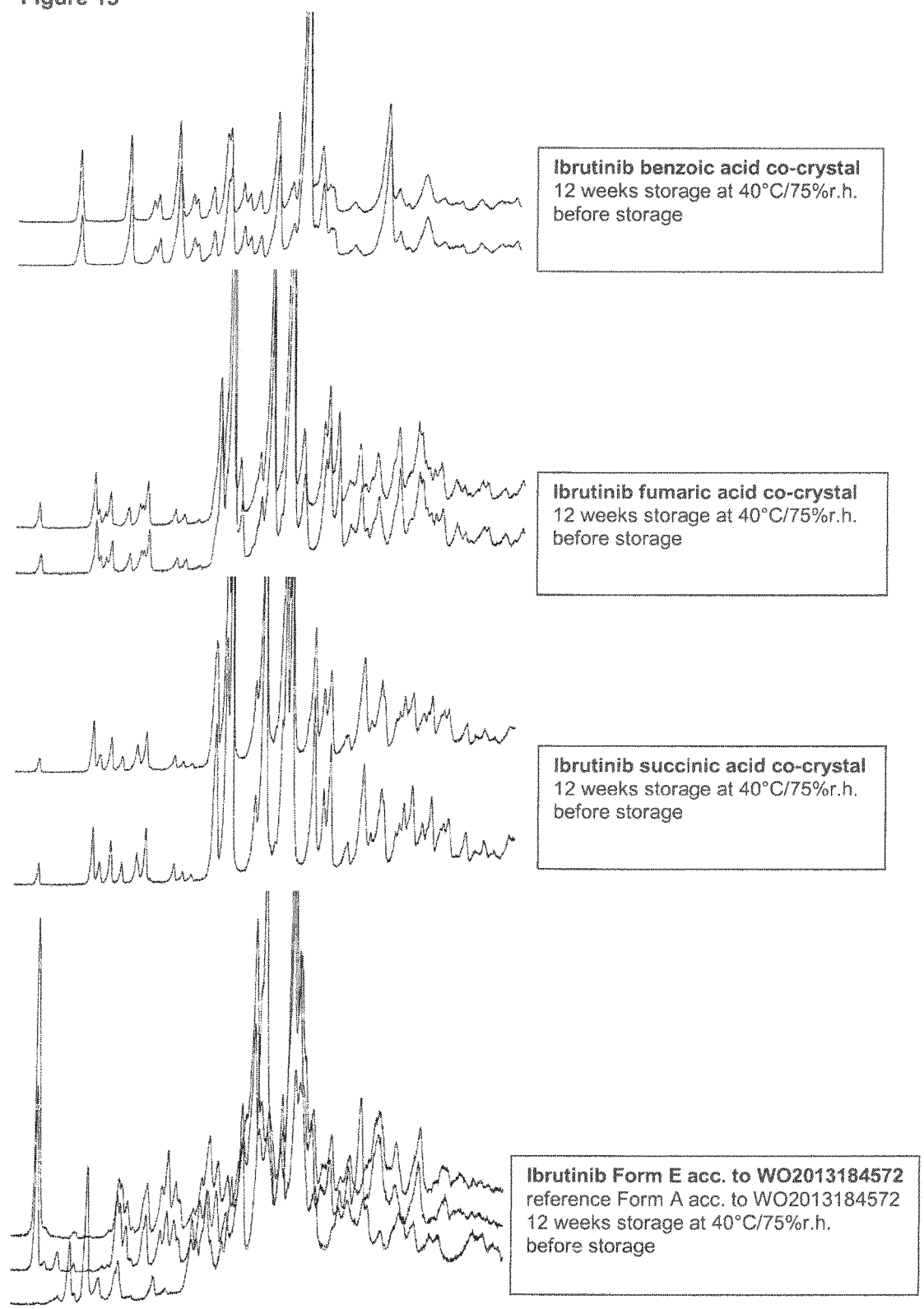
FIG. 15 shows the XRPD diffractograms of ibrutinib co-crystals compared to ibrutinib form E, each before and after storage for 12 weeks.

Ibrutinib Form E was stored for twelve weeks at a temperature of 40° C. and a relative humidity of 75%. Ibrutinib Form E transformed into ibrutinib Form A, as shown in FIG. 15 in comparison with the ibrutinib co-crystals according to the invention which remained stable during storage. This experiment demonstrates the surprisingly improved stability of the co-crystals of the invention over the prior art crystal form.

Comparative Example 2: Wettability

The wettability of the below compounds was determined by contact angle measurement. For this purpose, the substances were pressed (2 t*cm$^{-2}$) to a pellet. On each pellet were placed three water drops (2 µL) on three individual measurement points and the contact angle was measured with the apparatus OCA40 (DataPhysics Instruments) on two sides of the drop.

The determined values are given in table below.

| API Form | contact angle θ |
|---|---|
| Ibrutinib free base form A | 67.9° ± 2.1 |
| Ibrutinib fumaric acid | 56.8° ± 2.4 |
| Irbutinib succinic acid | incapable of measurement* |

*The contact angle of the co-crystal of ibrutinib and succinic acid was incapable of measurement because the wettability of this co-crystal is so high that the water drops immediately spread over the surface and the water sunk into the pellet.

A lower contact angle corresponds to an increase in wettability of the substance. An increased wettability facilitates granulation, in particular wet granulation of the substance. Therefore, as the co-crystals of the present invention have a lower contact angle and, thus, an increased wettability compared to ibrutinib free base, the co-crystals have advantageous properties with respect to further processing of the compound into pharmaceutical preparations.

The invention claimed is:

1. A co-crystal of ibrutinib and fumaric acid, wherein said ibrutinib fumatic acid co-crystal has characteristic X-ray power diffraction peaks at 9.9, 17.4, 18.7, 20.5 and 21.7 degrees 2-theta±0.2 degrees 2-theta.

2. A pharmaceutical preparation comprising the co-crystal of ibrutinib according to claim 1.

3. A method of treating chronic lymphocytic leukemia (CLL), small lymphocytic lymphoma (SLL) that are B-cell non-hodgkin lymphomas (NHL) and mantle cell lymphoma (MCL) in a patient in need thereof, said method comprising the step of administering an effective amount of the pharmaceutical preparation according to claim 2 to said patient.

4. The co-crystal of ibrutinib according to claim 1, wherein said ibrutinib fumaric acid co-crystal further has characteristic X-ray powder diffraction peaks at 6.5, 13.0, 18.2, 22.4 and 23.9 degrees 2-theta±0.2 degrees 2-theta.

* * * * *